US010370684B2

(12) United States Patent
Kawakami et al.

(10) Patent No.: US 10,370,684 B2
(45) Date of Patent: Aug. 6, 2019

(54) TREATMENT METHOD OF SACCHARIDE SOLUTION

(71) Applicant: MITSUBISHI CHEMICAL CORPORATION, Tokyo (JP)

(72) Inventors: Kiminori Kawakami, Kanagawa (JP); Yasuyo Saito, Kanagawa (JP); Takanao Matsumoto, Kanagawa (JP); Ryusuke Aoyama, Tokyo (JP); Shigeki Nitta, Kanagawa (JP); Masaru Utsunomiya, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/264,017

(22) Filed: Sep. 13, 2016

(65) Prior Publication Data

US 2016/0376616 A1 Dec. 29, 2016

Related U.S. Application Data

(63) Continuation of application No. PCT/JP2015/057384, filed on Mar. 12, 2015.

(30) Foreign Application Priority Data

Mar. 13, 2014 (JP) ................. 2014-050704
Jul. 10, 2014 (JP) ................. 2014-142566
Dec. 4, 2014 (JP) ................. 2014-246140

(51) Int. Cl.
*C12P 7/46* (2006.01)
*C13K 11/00* (2006.01)
*C13K 13/00* (2006.01)
*C12P 7/06* (2006.01)
*C13K 1/02* (2006.01)
*C13K 1/04* (2006.01)

(52) U.S. Cl.
CPC .......... *C12P 7/46* (2013.01); *C12P 7/06* (2013.01); *C13K 1/02* (2013.01); *C13K 1/04* (2013.01); *C13K 11/00* (2013.01); *C13K 13/00* (2013.01); *C13K 13/002* (2013.01); *Y02E 50/17* (2013.01)

(58) Field of Classification Search
None
See application file for complete search history.

(56) References Cited

U.S. PATENT DOCUMENTS

| 8,030,039 B1 | 10/2011 | Retsina et al. |
| 2003/0186398 A1 | 10/2003 | Schumann et al. |
| 2007/0254348 A1 | 11/2007 | Retsina et al. |
| 2011/0003352 A1 | 1/2011 | Retsina et al. |
| 2013/0011894 A1 | 1/2013 | Jönsson et al. |
| 2013/0022958 A1 | 1/2013 | Alriksson et al. |
| 2016/0177346 A1 | 6/2016 | Kawakami et al. |

FOREIGN PATENT DOCUMENTS

| JP | 2001-95594 A | 4/2001 |
| JP | 2005-270056 A | 10/2005 |
| JP | 2008-92910 A | 4/2008 |
| JP | 2009-213389 A | 9/2009 |
| JP | 2011-78327 A | 4/2011 |
| JP | 2012-161258 A | 8/2012 |
| JP | 2013-183704 A | 9/2013 |
| JP | 2014-20 A | 1/2014 |
| WO | WO 96/40970 A | 12/1996 |
| WO | WO 2007/146245 A2 | 12/2007 |
| WO | WO 2009/045654 A2 | 4/2009 |
| WO | WO 2011/080129 A2 | 7/2011 |
| WO | WO 2011/080130 A2 | 7/2011 |
| WO | WO2013/010271 A1 | 1/2013 |
| WO | WO 2015/002255 A1 | 1/2015 |

OTHER PUBLICATIONS

Jönsson et al. Biotechnol Biofuels. 2013; 6: 16.*
Parawira et al. Crit Rev Biotechnol. Mar. 2011;31(1):20-31.*
Ranatunga et al. Enzyme Microb Technol. Aug. 1, 2000;27(3-5):240-247.*
Alriksson et al. Bioresour Technol. Jan. 2011;102(2):1254-63.*
International Search Report dated May 26, 2015 in PCT/JP2015/057384 (with English translation).
Adnan Cavka, et al., "Effect of Sulfur Oxyanions on Lignocellulose-Derived Fermentation Inhibitors" Biotechnolgy and Bioengineering, vol. 108, No. 11, Nov. 2011, pp. 2592-2599.
I. S. Maddox, et al., "Production of n-Butanol by Fermentation of Wood Hydrolysate" Biotechnology Letters, vol. 5, No. 3, 1983, pp. 175-178.
Björn Alriksson, et al., "Improving the fermentability of Enzymatic Hydrolysates of Lignocellulose Through Chemical In-Situ Detoxification with Reducing Agents" Bioresource Technology, vol. 102, 2011, pp. 1254-1263.
Carina Van Zyl, et al., "Production of Ethanol from Sugar Cane Bagasse Hemicellulose Hydrolyzate by Pichia Stipitis" Applied Biochemistry and Biotechnology, vol. 17, 1988, pp. 357-369 and Cover pages.
Simona Larsson, et al., "Comparison of Different Methods for the Detoxification of Lignocellulose Hydrolyzates of Spruce" Applied Biochemistry and Biotechnology, vol. 77-79, 1999, pp. 91-103.

(Continued)

*Primary Examiner* — Christian L Fronda
(74) *Attorney, Agent, or Firm* — Oblon, McClelland, Maier & Neustadt, L.L.P.

(57) ABSTRACT

The invention relates to a method for treating a solution containing a saccharide comprising a heat treatment step of heating the saccharide solution at a temperature of 100° C. or higher and 180° C. or lower and a reduction step of reacting a reducing agent with the saccharide solution heated in the heat treatment step, a method for producing a treated saccharide solution using the treatment method, a treated saccharide solution obtained through treatment by the treatment method, a method for producing an organic compound comprising an organic-matter production step of obtaining an organic compound by causing a microorganism capable of producing organic matter to act on an organic raw material containing the treated saccharide solution and a method for culturing a microorganism using the treated saccharide solution as a carbon source.

10 Claims, No Drawings
Specification includes a Sequence Listing.

(56) References Cited

OTHER PUBLICATIONS

L. Olsson, et al., "Kinetics of Ethanol Production by Recombinant *Escherichia coli* KO11" Biotechnology and Bioengineering, vol. 45, 1995, pp. 356-365.
Office Action dated Jul. 10, 2018 in Japanese Patent Application No. 2016-507834, (with English translation), citing documents AX-AZ therein, 6 pages.
Satomiwa, "Let's prepare an invigorating pudding using lemon caramel sauce.", cookpad, URL:https://cookpad_com/recipe/1766990, 2018, (with English translation), 5 pages.
Maiko. E, "Let's prepare caramel sauce in a small quantity", cookpad, URL:https://cookpad.com/recipe/1894249, 2012, (with English translation), 4 pages.
"Science of Saccharides", Series of Food Ingredients, 1996, (with English translation), 15 pages.

* cited by examiner

TREATMENT METHOD OF SACCHARIDE SOLUTION

TECHNICAL FIELD

The present invention relates to a method for treating a solution containing a saccharide (saccharide solution) and a treated saccharide solution obtained by the treatment method. The invention also relates to a method for producing a treated saccharide solution, a method for producing an organic compound using the treated saccharide solution and a method for culturing a microorganism.

BACKGROUND ART

Fermentative processes of producing organic compounds from saccharides are widely used, and products obtained by the processes are used as various industrial raw materials.

Saccharides which are currently used as raw materials for the fermentative production processes and chemical conversion processes are saccharides derived from edible materials such as sugar cane, starch, sugar beet, corn, potatoes, cassava and sugar maple.

However, regarding the saccharides derived from edible materials, there are concerns that the prices of edible materials will soar as the world population increases and that edible materials will be in short supply due to bad weather or climate change. Also, use of edible materials for industrial raw materials, which is in competition with food use when food supply falls short, faces ethical criticism and concerns. Thus, development of a process of efficiently producing a saccharide solution from a non-edible material, a saccharide with lower purity containing impurities or the like or development of a process of efficiently converting the saccharide solution obtained as a raw material for the fermentative production into an industrial raw material is a task that should be accomplished in the future.

Methods for obtaining a saccharide solution from a non-edible material include a method in which cellulose and hemicellulose contained in a non-edible material are hydrolyzed into monosaccharides, for example hexoses such as glucose or pentoses such as xylose, using concentrated sulfuric acid (PTL 1), a method in which a non-edible material is subjected to pretreatment to improve the reactivity and then hydrolyzed through enzyme reaction (PTL 2), a hydrolysis method using subcritical or supercritical water or the like.

When these methods are used, however, cellulose and hemicellulose contained in a non-edible material are hydrolyzed to produce saccharides such as glucose and xylose, and degradation of the saccharides advances at the same time. The degradation of the saccharides generates carbonyl compounds as by-products apart from the saccharides. Specifically for example, carbonyl compounds such as aldehyde compounds, e.g. furfural, hydroxymethylfurfural, glycolaldehyde, syringaldehyde and formic acid, and ketone compounds, e.g. dihydroxyacetone and benzoquinone, are generated.

Of the carbonyl compounds apart from the saccharides, an aldehyde compound such as furfural and hydroxymethylfurfural and the like have the property of inhibiting the reaction in fermentative production processes using microorganisms. Specifically, an aldehyde compound and the like inhibit the multiplication of microorganisms or inhibit the fermentative production and thus decrease the yield of the fermentative production. Therefore, these compounds are called fermentation inhibitors and cause a large problem when a saccharide solution obtained from a non-edible material is used as a raw material for fermentation.

To solve this problem, methods for removing a fermentation inhibitor generated such as furfural have been studied, and for example, methods for removing a fermentation inhibitor through adsorption using various adsorbents such as active carbon and the like have been proposed (for example, PTL 3 and NPL 1). However, it is difficult to remove only the fermentation inhibitor selectively by the methods by adsorption, and drawbacks of the methods are that the saccharide concentration decreases because the saccharide is adsorbed and that these methods require costs for production and regeneration of the adsorbent. As other methods for removing a fermentation inhibitor, removal methods through reduction using a reducing agent such as sodium hyposulfite (NPLs 2 to 4 and PTL 4), removal methods using a synthetic resin (PTL 5) and the like have been proposed.

CITATION LIST

Patent Literature

PTL 1: JP-T-11-506934 (the term "JP-T" as used herein means a published Japanese translation of a PCT patent application)
PTL 2: JP-A-2001-95594
PTL 3: JP-A-2005-270056
PTL 4: WO2011/080129
PTL 5: JP-A-2011-78327

Non Patent Literature

NPL 1: Biotechnology Letters vol. 5 No. 3, P175, 1983
NPL 2: Biotechnology and Bioengineering, vol. 108, No11, P2592, 2011
NPL 3: Cavka A et al., Bioresource Technology, vol. 102, P1254, 2011
NPL 4: Bioresource Technology, vol. 102, P1254, 2011

SUMMARY OF INVENTION

Technical Problem

The removal methods through reduction using a reducing agent are highly capable of removing a fermentation inhibitor and are effective methods especially because aldehyde compounds in general, including water-soluble aldehydes which are difficult to remove by other methods, can be removed.

Here, a saccharide solution is generally sterilized before the fermentative production process to kill/reduce or remove microorganisms which cause reaction other than the target reaction. In particular, a saccharide solution obtained from a non-edible material often contains a large amount of nutrients necessary for the growth of microorganisms and thus sometimes significantly reduces the yield of the target product when subjected to the fermentative production process without sterilization. Thus, it is considered to be preferable to sterilize such a saccharide solution.

A simple, efficient sterilization method that is generally used is heat sterilization in which a saccharide solution is generally heated.

However, when the saccharide solution is subjected to both of the treatment with a reducing agent and heat sterilization, the yield of the target product does not increase, and the effects expected from the treatment methods are not always obtained.

The invention has been made in view of the above problems. A first object of the invention is: to provide a method for treating a saccharide solution which is subjected to a fermentative production process and a chemical conversion process of a chemical product when an organic compound is produced from a saccharide, wherein the method has excellent production efficiency and can facilitate the process design; and to provide a method for producing an organic compound using a saccharide solution obtained by the method.

Moreover, in addition to the problem that an aldehyde compound contained in a saccharide solution obtained from a non-edible material is a cause of strong inhibition of fermentation, there is a problem of coloration of the product when an organic compound is produced through a chemical conversion process from a saccharide solution obtained from a non-edible material because the saccharide solution contains a carbonyl compound apart from the saccharide. Thus, it is desired that the amount of the carbonyl compound except for the saccharide contained in the saccharide solution is reduced as much as possible.

However, it is difficult to remove only the carbonyl compound except for the saccharide selectively by the removal methods using wood carbide or active carbon, and there are problems of a decrease in the saccharide concentration due to the adsorption of the saccharide and the costs for production and regeneration of wood carbide or active carbon. Moreover, problems of the removal methods using a synthetic resin agent are that the removal is achieved by chromatography and the process design is thus restricted.

Also, these removal methods have problems because it is difficult to remove a water-soluble aldehyde compound, such as glycolaldehyde, of the above aldehyde compounds by the methods and because the amount of the carbonyl compound except for the saccharide contained in the saccharide solution does not decrease.

By the methods for removing an aldehyde compound through reduction using a reducing agent, aldehyde compounds in general including water-soluble aldehyde compounds can be removed. However, because a metal salt of sulfurous acid, hyposulfurous acid or the like is used as the reducing agent in the methods, the metal salt content of the saccharide solution increases after the removal of the aldehyde compound by reduction. In particular, a saccharide solution obtained from a non-edible material originally contains a large amount of a metal salt in general, and thus the metal salt content is further increased by the removal by reduction. Accordingly, the metal derived from the metal salt is contained in the subsequent fermentation process, purification process of the fermentation liquid and the like, and a problem arises because the removal of the metal salt imposes additional burden on the entire process in case where the reduction in the metal amount is required when the fermentation product is purified by distillation.

The invention has been made in view of the above problems. A second object of the invention is: to provide a method for purifying a saccharide solution having excellent production efficiency which can sufficiently remove a carbonyl compound except for the saccharide contained in a saccharide solution subjected to a fermentative production process and a chemical conversion process of a chemical product when an organic compound is produced from a saccharide and which can facilitate the process design; and to provide a method for producing an organic compound using a saccharide solution obtained by the method.

Solution to Problem

As a result of investigation, the inventors have found that the first object can be achieved by combining sterilization and treatment with a reducing agent in accordance with certain procedures, and the inventors have reached the invention.

That is, the first gist of the invention resides in the method for treating a saccharide solution, the method for producing a treated saccharide solution, the treated saccharide solution, the method for producing an organic compound and the culture method described below.

[1-1] A method for treating a solution containing a saccharide (hereinafter referred to as "a saccharide solution"), comprising: a heat treatment step of heating the saccharide solution at a temperature of 100° C. or higher and 180° C. or lower; and a reduction step of reacting a reducing agent with the saccharide solution heated in the heat treatment step.

[1-2] A method for treating a solution containing a saccharide containing a monosaccharide and/or a disaccharide as a main component (hereinafter referred to as "a saccharide solution"), comprising: a heat treatment step of heating the saccharide solution at a temperature of 100° C. or higher and 180° C. or lower; and a reduction step of reacting a reducing agent with the saccharide solution heated in the heat treatment step.

[1-3] The method for treating a saccharide solution according to the [1-1] or [1-2] above, wherein the pH of the saccharide solution in the reduction step is 2 or more and 8 or less.

[1-4] The method for treating a saccharide solution according to any one of the [1-1] to [1-3] above, wherein the temperature of the saccharide solution in the reduction step is 20° C. or higher and 70° C. or lower.

[1-5] The method for treating a saccharide solution according to any one of the [1-1] to [1-4] above, wherein the reducing agent is at least one selected from sulfurous acid compounds, hyposulfurous acid compounds and thiosulfuric acid compounds.

[1-6] The method for treating a saccharide solution according to any one of the [1-1] to [1-5] above, wherein the amount of the reducing agent used is 0.05 mass % or more and 2.0 mass % or less based on the mass of the saccharide contained in the saccharide solution.

[1-7] The method for treating a saccharide solution according to any one of the [1-1] to [1-6] above, wherein the heating period of the saccharide solution in the heat treatment step is one minute or longer and 20 hours or shorter.

[1-8] A method for producing a treated saccharide solution by treating a solution containing a saccharide (hereinafter referred to as "a saccharide solution"), wherein the treatment method is the method for treating a saccharide solution according to any one of the [1-1] to [1-7] above.

[1-9] A treated saccharide solution obtained through treatment by the method for treating a saccharide solution according to any one of the [1-1] to [1-7] above or a treated saccharide solution obtained by the production method according to the [1-8] above.

[1-10] A method for producing an organic compound, comprising:
a heat treatment step of heating a solution containing a saccharide (hereinafter referred to as "a saccharide solution") at a temperature of 100° C. or higher and 180° C. or lower;
a reduction step of reacting a reducing agent with the saccharide solution heated in the heat treatment step; and
an organic-matter production step of obtaining an organic compound by causing a microorganism capable of producing organic matter to act on an organic raw material containing the saccharide solution which has undergone the reduction step.

[1-11] A method for producing an organic compound, comprising an organic-matter production step of obtaining an organic compound by causing a microorganism capable of producing organic matter to act on an organic raw material containing the treated saccharide solution according to the [1-9] above.

[1-12] A method for culturing a microorganism capable of producing organic matter, wherein the treated saccharide solution according to the [1-9] above is used as a carbon source.

As a result of extensive investigation to achieve the second object, the inventors have found that the second object can be achieved by reacting a reducing agent containing sulfur having an oxidation number in a specific range and ammonium ion with a saccharide solution, thereby reducing a carbonyl compound except for the saccharide contained in the saccharide solution, and the inventors have thus completed the invention. That is, the second gist of the invention resides in the method for treating a saccharide solution, the method for producing a treated saccharide solution, the reduced saccharide solution, the method for producing an organic compound and the culture method described below.

[2-1] A method for treating a saccharide solution using a reducing agent, wherein the reducing agent is an ionic compound, the ionic compound contains an anion containing one or more kinds of sulfur having an oxidation number selected from −2, +2, +3 and +4 and ammonium ion, and the reducing agent reduces a carbonyl compound except for a saccharide contained in the saccharide solution.

[2-2] The method for treating a saccharide solution according to the [2-1] above, wherein the anion is at least one selected from sulfite ion, hydrogen sulfite ion, hyposulfite ion, thiosulfate ion and sulfide ion.

[2-3] The method for treating a saccharide solution according to the [2-1] or [2-2] above, wherein the ratio by mole of the reducing agent to the carbonyl compound except for the saccharide is 0.05 or more and 2.0 or less.

[2-4] The method for treating a saccharide solution according to any one of the [2-1] to [2-3] above, wherein the saccharide is a saccharide containing a monosaccharide having three or more and seven or less carbon atoms as a component.

[2-5] The method for treating a saccharide solution according to any one of the [2-1] to [2-4] above, wherein the saccharide solution is a saccharide solution derived from a non-edible material.

[2-6] The method for treating a saccharide solution according to any one of the [2-1] to [2-5] above, wherein the carbonyl compound is at least one selected from aldehyde compounds and ketone compounds.

[2-7] A method for producing a treated saccharide solution by treating a saccharide solution using a reducing agent,
wherein the reducing agent is an ionic compound,
the ionic compound comprises: an anion containing one or more kinds of sulfur having an oxidation number selected from −2, +2, +3 and +4; and ammonium ion, and
the reducing agent reduces a carbonyl compound except for a saccharide contained in the saccharide solution.

[2-8] A reduced saccharide solution obtained through treatment by the method for treating a saccharide solution according to any one of the [2-1] to [2-6] above or a reduced saccharide solution obtained by the production method according to the [2-7] above.

[2-9] A method for producing an organic compound, comprising a step of obtaining an organic compound by causing a microorganism capable of producing organic matter to act on an organic raw material containing the reduced saccharide solution according to the [2-8] above in a reaction solution (hereinafter referred to as "an organic-matter production step").

[2-10] The method for producing an organic compound according to the [2-9] above, wherein the organic compound is at least one selected from alcohols, amines, carboxylic acids and phenols.

[2-11] The method for producing an organic compound according to the [2-9] or [2-10] above, wherein the organic compound is an aliphatic alcohol having 2 to 10 carbon atoms.

[2-12] The method for producing an organic compound according to the [2-9] or [2-10] above, wherein the organic compound is an aliphatic carboxylic acid having 2 to 10 carbon atoms.

[2-13] A method for culturing a microorganism capable of producing organic matter, wherein the reduced saccharide solution according to the [2-8] above is used as a carbon source.

Advantageous Effects of Invention

According to the first method for treating a saccharide solution of the invention, the amount of a carbonyl compound except for the saccharide can be reduced while the sterilized state is maintained. Thus, when the saccharide solution obtained by the method is used for a fermentative production process using a microorganism, the yield of the target organic compound can be increased.

The first treated saccharide solution of the invention can improve the production efficiency of a microorganism in the production of an organic compound through fermentative production.

By the first method for producing an organic compound of the invention, a desired organic compound can be produced with high production efficiency through relatively simple treatment.

By the first culture method of the invention, the amount of a carbonyl compound and the like except for the saccharide in a fermentative production process can be reduced. Thus, the multiplication amount and the multiplication rate of a microorganism can be increased, and the fermentative productivity can be improved.

According to the second method for treating a saccharide solution of the invention, the amount of a carbonyl compound except for the saccharide can be reduced without increasing the metal content of the saccharide solution. Thus, when the saccharide solution obtained by the method is used for a fermentative production process using a microorganism, the yield of the target organic compound can be increased. Also, it is not only possible to prevent the metal content from being increased by the treatment of the saccharide solution but also to degrade an ionic compound used as a reducing agent by thermal decomposition or the like, thereby reducing the burden imposed by the step of removing a metal salt.

The second reduced saccharide solution of the invention can improve the production efficiency of a microorganism in the production of an organic compound through fermentative production and prevent the coloration of the organic compound, which is the product, when used for a chemical conversion process.

By the second method for producing an organic compound of the invention, a desired organic compound can be produced with high production efficiency through relatively simple treatment.

By the second culture method of the invention, the amount of a carbonyl compound except for the saccharide in a fermentative production process can be reduced. Thus, the multiplication amount and the multiplication rate of a microorganism can be increased, and the fermentative productivity can be improved.

DESCRIPTION OF EMBODIMENTS

The invention is explained specifically below. However, the invention should not be limited to the following embodiments and can be modified and carried out in various manners within the scope of the gist of the invention. The term "organic compound" and the term "organic matter" used below have the same meanings.

<<Invention 1>>

The method for treating a saccharide solution, the method for producing a treated saccharide solution, the treated saccharide solution, the method for producing an organic compound and the culture method according to invention 1 are described in detail below.

<Invention 1-1: Treatment Method of Saccharide Solution>

Invention 1-1 of the invention is characterized by including a step of heating a solution containing a saccharide (hereinafter "a saccharide solution") at a temperature of 100° C. or higher and 180° C. or lower (a heat treatment step) and a step of reacting a reducing agent with the saccharide solution heated (a reduction step).

The saccharide solution of invention 1-1 and the "saccharide solution" used in invention 1-2, invention 1-3 and invention 1-4 (inventions 1-1 to 1-4 are sometimes called "invention 1" together) described below mean a solution containing a saccharide, preferably an aqueous solution containing a saccharide. The explanation is made below in order from the saccharide contained in the saccharide solution.

(Saccharide)

The saccharide contained in the saccharide solution used in invention 1 is not particularly limited, and so-called saccharides in general can be used. However, a saccharide which a microorganism can use as a carbon source is preferable. Specific examples thereof include: monosaccharides having three carbon atoms (trioses) such as glyceraldehyde; monosaccharides having four carbon atoms (tetroses) such as erythrose, threose and erythrulose; monosaccharides having five carbon atoms (pentoses) such as ribose, lyxose, xylose, arabinose, deoxyribose, xylulose and ribulose: monosaccharides having six carbon atoms (hexoses) such as allose, talose, gulose, glucose, altrose, mannose, galactose, idose, fucose, fuculose, rhamnose, psicose, fructose, sorbose and tagatose; monosaccharides having seven carbon atoms (heptoses) such as sedoheptulose; disaccharides such as sucrose, lactose, maltose, trehalose, turanose and cellobiose; trisaccharides such as raffinose, melezitose and maltotriose: oligosaccharides such as fructo-oligosaccharides, galacto-oligosaccharides and mannan-oligosaccharides: polysaccharides such as starch, dextrin, cellulose, hemicellulose, glucan and pentosan; and the like.

The saccharide solution used in invention 1 may contain one of the saccharides alone or may contain two or more thereof.

The saccharide solution used in invention 1 preferably contains a monosaccharide and/or a disaccharide of the above saccharides as a main component. That is, the saccharide solution used in invention 1 is preferably a solution containing saccharides containing a monosaccharide and/or a disaccharide as a main component. The term "as a main component" here means that the content thereof is 50 mol % or more of the total amount of the saccharides contained in the saccharide solution, preferably 70 mol % or more, more preferably 80 mol % or more, further preferably 90 mol % or more. The upper limit thereof is 100 mol %.

Of the saccharides used in invention 1, saccharides containing a monosaccharide having three or more and seven or less carbon atoms as a component are preferable. The saccharides containing a monosaccharide having three or more and seven or less carbon atoms mean monosaccharides having three or more and seven or less carbon atoms and disaccharides and polysaccharides containing a monosaccharide having three or more and seven or less carbon atoms as a component. Of the saccharides, hexoses, pentoses and disaccharides containing a hexose or a pentose as a component are more preferable. This is because these saccharides are structural components of plants in the natural world and thus are abundant and because the raw materials are easy to obtain.

As the hexoses, glucose, fructose, mannose and galactose are preferable, and glucose is more preferable. As the pentoses, xylose and arabinose are preferable, and xylose is more preferable. As the disaccharides, sucrose is preferable. Glucose, xylose and sucrose are main structural components of plants in the natural world, and thus the raw materials are easy to obtain.

(Origin and Production Method of Saccharide Solution)

The method for producing the saccharide solution used in invention 1 is not particularly limited, but examples thereof include a production method in which one or more of the saccharides are dissolved in water and a production method in which a raw material containing the saccharide as a component (hereinafter sometimes referred to as "a saccharide raw material") is degraded into the constituent unit saccharide. The saccharide raw material is not particularly limited, but specific examples thereof include polysaccharides such as cellulose, hemicellulose and starch, plants containing a polysaccharide as a component and the like. Also, a saccharified solution of starch, molasses or the like is used, and specific examples thereof include saccharide solutions obtained by squeezing a plant such as sugar cane, sugar beet or sugar maple.

The saccharide raw materials can be classified into "edible materials" and "non-edible materials" by whether or not the materials can be used for food.

Edible materials include sugar cane, starch, sugar beet, corn, potatoes, cassava, sugar maple and the like.

Non-edible materials include specifically bagasse, switchgrass, napier grass, ravennagrass, corn stover, rice straw, wheat straw, rice bran, trees, wood, vegetable oil cake, bamboo grass, bamboo, pulp, waste paper, food waste, marine products residue, livestock waste and the like.

Unlike the edible materials, the non-edible materials do not compete with food uses and are often disposed of or incinerated in general. Thus, the non-edible materials are preferable in view of the stable supply and effective utilization of resources.

The method for obtaining a saccharide from the saccharide raw material is not particularly limited, but examples thereof include the following methods: a method in which an aqueous starch solution is hydrolyzed with dilute sulfuric acid; a production method in which an aqueous starch solution is enzymatically degraded using an enzyme; a method in which cellulose or hemicellulose is hydrolyzed into monosaccharides, for example hexoses such as glucose or pentoses such as xylose, using concentrated sulfuric acid; a method in which a saccharide raw material is subjected to pretreatment to improve the reactivity and then hydrolyzed using enzyme reaction, subcritical water, supercritical water or the like; and other methods. Moreover, exhaust molasses which remains after recovering sugar from molasses generated in a sugar production step can also be used as a saccharide solution.

The saccharide solution used in the invention is preferably a saccharide solution obtained by hydrolyzing a polysaccharide contained in a saccharide raw material by any of the above methods. The saccharide contained in the saccharide solution thus obtained preferably contains a monosaccharide and/or a disaccharide as a main component and more preferably contains a monosaccharide as a main component.

In the saccharide solution used in invention 1, a part of a polysaccharide, an oligosaccharide and the like sometimes remains without having being degraded.

The concentration of the saccharide contained in the saccharide solution in invention 1 varies considerably according to the origin of the saccharide solution, the kind of saccharide contained and the like and is not particularly limited. However, considering the productivity of the fermentative production process and the chemical conversion process, when the saccharide contains a monosaccharide and/or a disaccharide as a main component, the total concentration of the saccharides containing a monosaccharide and a disaccharide is generally 0.1 mass % or more, preferably 2 mass % or more and is generally preferably 60 mass % or less, preferably 50 mass % or less.

The saccharide solution used in invention 1 is a solution containing the saccharide, preferably an aqueous solution, and may contain another component in addition to water and the saccharide. The other component is not particularly limited, but for example, the saccharide solution may contain, in addition to the saccharide, by-products and impurities which are generated when the saccharide containing a monosaccharide and/or a disaccharide as a main component is obtained from a saccharide raw material. Specific examples thereof are: the carbonyl compounds except for the saccharide and the alcohol compounds such as aliphatic conjugated alcohols which are described below; lignin-derived phenolic compounds; alkali metal compounds such as alkali metal salts; alkaline earth metal compounds such as alkaline earth metal salts; nitrogen compounds, sulfur compounds, halogen compounds, sulfate ion and the like.

The saccharide solution used in invention 1 is not particularly limited as long as it is a solution containing the saccharide described above, but a solid material derived from lignin or the like is preferably removed through filtration, adsorption or the like. Also, the saccharide solution used in invention 1 can be used after reducing the saccharide concentration by diluting with water according to the purpose of use or used after increasing the saccharide concentration by adding an additional saccharide or through concentration.

(Carbonyl Compound Except for Saccharide)

The saccharide solution used in invention 1 generally contains a carbonyl compound which is generated during the step of producing the saccharide solution and during the storage in addition to the saccharide. The carbonyl compound is not particularly limited as long as the carbonyl compound has a carbonyl group in the structure, and the carbonyl compound may be an aliphatic carbonyl compound or a carbonyl compound having an aromatic group. Carbonyl compounds having one or more carbon atoms and preferably 20 or less carbon atoms, more preferably 16 or less carbon atoms, further preferably 12 or less carbon atoms are preferable. This is because the carbonyl compounds in the range are relatively highly soluble in water and are often contained in a saccharide solution, especially in an aqueous solution containing a saccharide. Specific examples of such a carbonyl compound include: aldehyde compounds such as furfural, hydroxymethylfurfural, formic acid, glycolaldehyde, glyoxal, hydroxybenzaldehyde, syringaldehyde, vanillin, isovanillin, ortho-vanillin and coniferil aldehyde: ketone compounds such as 1,4-benzoquinone: unsaturated ester compounds such as methyl acrylate and ethyl acrylate, preferably unsaturated conjugated ester compounds; and the like. These compounds sometimes strongly inhibit fermentation in invention 1-3 and invention 1-4 below.

Glycolaldehyde, glyoxal and the like of the aldehyde compounds are water-soluble aldehyde compounds and are difficult to remove by physical adsorption or the like. Thus, the method of invention 1 is particularly useful when a saccharide solution containing a large amount of these aldehyde compounds is used.

The carbonyl compound except for the saccharide contained in the saccharide solution is sometimes simply referred to as "a carbonyl compound" below.

The inventors have found that the carbonyl compound except for the saccharide reduces/decreases the production amount, the accumulation amount and the production rate of a useful compound in the step of producing the useful compound from a saccharide solution by fermentation. Hereinafter, a substance having the effect is called "a fermentation inhibitor" in general. A saccharide solution containing the fermentation inhibitor decreases the multiplication amount and the multiplication rate in the step of culturing a microorganism.

(Heat Treatment Step)

Invention 1-1 of invention 1 includes a step of heating a saccharide solution (a heat treatment step) and a step of reacting a reducing agent with the saccharide solution heated in the step (a reduction step). The steps are described below.

In general, the heat treatment step is a step for killing/reducing or removing a microorganism or the like which causes reaction other than the target reaction when the saccharide solution obtained in invention 1 is used in a fermentative production process, namely a step for sterilization. The heat treatment step is conducted by holding the saccharide solution at a specific heating temperature.

The heating temperature of the heat treatment step is 100° C. or higher and 180° C. or lower. The lower limit is preferably 110° C. or higher, more preferably 115° C. or higher, and the upper limit is preferably 160° C. or lower, more preferably 150° C. or lower, further preferably 140° C. or lower. This is because by heating at a temperature in the range, the effect of sterilization can be obtained sufficiently.

In addition, the saccharide can be inhibited from being degraded by heating, and the fermentation inhibitor can be inhibited from increasing in amount. A heating temperature at which the effect of the sterilization can be obtained sufficiently can be selected appropriately from the range. In particular, a heating temperature not higher than the upper limit is preferable because the monosaccharide and the disaccharide contained in the saccharide solution are not degraded and converted into hydroxymethylfurfural (HMF), a carboxylic acid or the like.

The heating conditions are not particularly limited as long as the effect of the sterilization can be obtained sufficiently. The saccharide solution may be heated at a constant temperature or heated at different temperatures, and when the saccharide solution is heated at different temperatures, the difference between the temperatures and the temperature gradient may be optionally determined.

The pH of the saccharide solution is preferably adjusted before the heat treatment is conducted. A preferable pH range is 6 to 8, and the pH is preferably adjusted in the range by appropriately adding an acid such as hydrochloric acid or sulfuric acid or a base such as ammonia, sodium hydroxide or potassium hydroxide. A pH value in the range is preferable because the degradation of the saccharide is not promoted and the saccharide concentration can be maintained.

The treatment period of the heat treatment step is not particularly limited as long as the effect of the sterilization can be obtained, but the treatment period is generally one minute or longer, preferably three minutes or longer, more preferably five minutes or longer and is generally 20 hours or shorter, preferably five hours or shorter, more preferably one hour or shorter. This is because sufficient effect of the sterilization can be obtained in the treatment period within the range. A treatment period in which the effect of the sterilization can be obtained sufficiently can be selected appropriately.

The means for heating the saccharide solution is not particularly limited as long as the saccharide solution can be heated to the heating temperature, and the means can be selected appropriately in accordance with the amount and the composition of the saccharide solution to be treated. Specific examples thereof include a batch method for heating the saccharide solution using a tank or the like and a continuous heating method using a continuous sterilizer or the like while causing the saccharide solution to flow in. Also, examples of the heating method include a method for heating the saccharide solution by directly introducing a heating medium such as steam into the device such as a tank or a continuous sterilizer, a method for heating the saccharide solution by bringing the saccharide solution into indirect contact with a heating medium such as steam using a heat exchanger provided in the device and the like. When a large amount is treated, the continuous heating method of the examples is preferable because the treatment efficiency is good.

As described above, the saccharide solution to be subjected to the heating step is preferably obtained by hydrolyzing a polysaccharide contained in a saccharide raw material. This is because the reduction step is preferably conducted following the heating step. According to the investigation of the inventors, it has been elucidated that the raw material cannot sufficiently maintain its sterilized state achieved by the heating step when a step of hydrolyzing a polysaccharide, long-time storage or the like is conducted after the heating step and that as a result, the efficiency of fermentative production of an organic compound by the target microorganism decreases. It has been found that even when an attempt is made to maintain the sterilized state by adjusting the pH or the like of the storage state, its effect is not sufficient. Thus, it is preferable to conduct the heating step and the reduction step in succession. For example, the reduction step is preferably conducted within one or two days of the heating step.

(Reduction Step)

The reduction step is a step for the purpose of reducing the amount of a carbonyl compound except for the saccharide which is generally contained in the saccharide solution by reacting a reducing agent with the saccharide solution which has undergone the heat treatment step.

It is presumed that the carbonyl compound except for the saccharide contained in the saccharide solution is generally converted into a substance which inhibits fermentation less than the carbonyl compound through the reduction step. Specifically, it is presumed that a reaction adduct of the carbonyl compound and the reducing agent described below (hereinafter sometimes referred to as "a reduction product") is generated.

As the specific reduction product, it is presumed that when an aldehyde compound is subjected to the reduction step using a sulfite or a hyposulfite as the reducing agent for example, the aldehyde compound is converted into $\alpha$-hydroxysulfonate.

By subjecting the saccharide solution to the heat treatment step and the reduction step, the saccharide solution can be sterilized, and the amount of the fermentation inhibitor in the saccharide solution can be reduced. Thus, the fermentation process can be conducted without decreasing the multiplication rate and the multiplication amount in the fermentative production process of an organic compound and the step of culturing a microorganism.

The reducing agent used in the reduction step is not particularly limited as long as the carbonyl compound content can be reduced. Examples thereof include sulfurous acid compounds such as sodium sulfite, sodium hydrogen sulfite, potassium sulfite, potassium hydrogen sulfite, calcium sulfite, ammonium sulfite, ammonium hydrogen sulfite and sulfurous acid solution: hyposulfurous acid compounds such as sodium hyposulfite, potassium hyposulfite, calcium hyposulfite and ammonium hyposulfite; thiosulfuric acid compounds such as sodium thiosulfate, potassium thiosulfate, calcium thiosulfate and ammonium thiosulfate; sulfides such as sodium sulfide, potassium sulfide, calcium sulfide and ammonium sulfide: reducing organic matter such as ascorbic acid, cysteine, diethanolamine and triethanolamine; and the like.

Of these compounds, sulfurous acid compounds, hyposulfurous acid compounds and thiosulfuric acid compounds are preferable because the compounds are easily obtained and easily handled.

As long as the effects of invention 1 are not impaired, one of the reducing agents may be used, or a combination of two or more of the reducing agents may be used. Also, the ratio of the reducing agents used is not limited.

The conditions of the reduction are not particularly limited as long as the reduction step is conducted after the heat treatment step and the carbonyl compound content of the saccharide solution can be reduced while the sterilized state achieved by the heat treatment is maintained.

It is thought that the fermentation inhibitor such as a carbonyl compound forms a reaction adduct with the reducing agent, namely a reduction product, and thus is removed from the saccharide solution. However, it is thought that the reduction product is for example degraded under the heating conditions for sterilizing the saccharide solution because the reduction product is unstable under high-temperature conditions.

By the production method of the invention, a carbonyl compound which inhibits fermentation can be removed while the sterilized state is maintained. Thus, it is believed that an organic compound can be produced efficiently even from a saccharide solution, preferably a saccharide solution containing a large amount of a carbonyl compound derived from a non-edible material.

In this regard, the saccharide contained in the saccharide solution also has a carbonyl group such as an aldehyde group and thus reacts with the reducing agent, like the carbonyl compound. That is, a reaction product of the saccharide and the reducing agent is sometimes generated. However, as long as no problem arises in the step of producing an organic compound by fermentation and the step of culturing a microorganism, which are described below, the conditions of the reduction are not limited. Accordingly, it is preferable to select selective reaction conditions under which the amount of the carbonyl compound except for the saccharide can be reduced and under which the saccharide such as glucose or xylose does not easily react with the reducing agent of invention 1.

The treatment temperature of the reduction step of invention 1 is not particularly limited but is generally 20° C. or higher and 100° C. or lower, preferably 80° C. or lower, further preferably 70° C. or lower. By conducting the reduction step at a temperature within the range, the degradation of the reducing agent and the reduction product can be inhibited, and the amount of the carbonyl compound except for the saccharide, which is a fermentation inhibitor, can be reduced without causing the saccharide to react with the reducing agent.

The pH of the saccharide solution in the reduction step is not particularly limited, but the pH is generally 2 or more, preferably 3 or more, more preferably 4 or more and is generally 8 or less, preferably 7 or less, in order that the degradation of the reducing agent and the reduction product can be inhibited and the amount of the fermentation inhibitor such as the carbonyl compound can be reduced. After the heat treatment, the pH is sometimes acidic, and specifically, the pH is sometimes about 3 to 6. In this case, the pH may be appropriately adjusted by adding an acid such as hydrochloric acid or sulfuric acid or a base such as ammonia, sodium hydroxide or potassium hydroxide, but pH in the above range is preferable because the degradation of the reducing agent is not promoted and the reduction advances efficiently.

The amount of the reducing agent used in the reduction step is determined by the conditions such as the concentration of the fermentation inhibitor in the saccharide solution, specifically the concentration of the carbonyl compound, the kind of the reducing agent used, the reaction temperature, the reaction style and the amount of the saccharide solution to be treated and by the desired results of the reaction such as the efficiency of the removal of the fermentation inhibitor, inhibition of the reaction between the saccharide and the reducing agent and decrease in the amount of the unreacted reducing agent. Thus, the amount of the reducing agent is not particularly limited.

The amount of the reducing agent used, based on the mass of the saccharide contained in the saccharide solution, is generally 0.05 mass % or more, preferably 0.1 mass % or more and is generally 2.0 mass % or less, preferably 1.5 mass % or less.

The treatment period of the reduction step is determined by the conditions such as the amount and the concentration of the fermentation inhibitor in the saccharide solution, specifically the concentration of the carbonyl compound, the kind of the reducing agent used, the reaction temperature, the reaction style and the amount of the saccharide solution to be treated and by the desired results of the reaction such as the efficiency of the removal of the fermentation inhibitor and inhibition of the reaction between the saccharide and the reducing agent. Thus, the treatment period is not particularly limited.

Specifically, the treatment period is generally one minute or longer, preferably 10 minutes or longer, more preferably 30 minutes or longer after the reducing agent has been added and the temperature of the saccharide solution has reached the treatment temperature. The upper limit thereof is not particularly limited as long as the fermentation inhibitor is removed sufficiently but is generally 48 hours or shorter, preferably 24 hours or shorter, more preferably 10 hours or shorter.

When the treatment period is within the range, the amount of the fermentation inhibitor such as the carbonyl compound can be reduced sufficiently, and the generation of the reaction product of the saccharide and the reducing agent can be inhibited.

A solvent can be used in the reduction step. The kind thereof is not particularly limited, but water is generally used. An organic solvent may be used as a cosolvent. However, an organic solvent mixed in the aqueous phase may inhibit fermentation and requires a step of separating the organic solvent before the fermentative production or the step of culturing a microorganism. Thus, it is desirable that the saccharide solution in the form of aqueous solution is directly subjected to the reduction step.

<Invention 1-2: Treated Saccharide Solution>

Because the saccharide solution is sterilized and the amount of the carbonyl compound except for the saccharide contained in the saccharide solution is reduced by the heat treatment and the reduction in invention 1-1, the concentration of the carbonyl compound in the saccharide solution obtained is generally lower than the concentration in the original saccharide solution. In this regard, the saccharide solution which has been subjected to the heat treatment step and the reduction step is sometimes referred to as "a treated saccharide solution" below.

By reacting the carbonyl compound with the reducing agent of invention 1, the efficiencies of the multiplication of a microorganism and of the fermentative production of a useful compound can be improved in the fermentation process described below.

The treated saccharide solution of invention 1-2 may contain the reaction product of the carbonyl compound and the reducing agent, and specifically, when the carbonyl compound is an aldehyde compound, the treated saccharide solution may contain corresponding α-hydroxysulfonate or the like.

The treated saccharide solution of invention 1-2 may be further treated appropriately with an ion exchange resin, active carbon or a synthetic resin or by a method such as hydrogenation according to the need.

<Invention 1-3: Production Method of Organic Compound>

Various organic compounds can be produced by causing a microorganism capable of producing organic matter to act on the treated saccharide solution of invention 1-2.

(Microorganism Capable of Producing Organic Matter)

The microorganism used in invention 1-3 is not particularly limited as long as the microorganism is capable of producing organic matter.

The "microorganism capable of producing organic matter" in invention 1-3 means a microorganism that can generate and accumulate organic matter in a culture medium when the microorganism is cultured in the culture medium.

(Organic Compound)

The organic compound that the microorganism produces is not limited as long as the microorganism can generate and accumulate the organic compound in a culture medium. Specific examples include alcohols such as ethanol, propanol, butanol, 1,2-propanediol, 1,3-propanediol, 1,3-butanediol, 2,3-butanediol, 1,4-butanediol, 1,5-pentanediol, 1,6-hexanediol, glycerol, erythritol, xylitol and sorbitol; amines such as 1,5-pentamethylenediamine and 1,6-hexamethylenediamine; carboxylic acids such as acetic acid, butyric acid, glycolic acid, lactic acid, 3-hydroxypropionic acid, pyruvic acid, succinic acid, fumaric acid, malic acid, oxaloacetic acid, cis-aconitic acid, citric acid, isocitric acid, 2-oxoglutaric acid, 2-oxoisovaleric acid, glutaric acid, itaconic acid, adipic acid, levulinic acid, quinic acid, shikimic acid, acrylic acid and methacrylic acid; amino acids such as alanine, valine, leucine, isoleucine, lysine, arginine, methionine, histidine, cysteine, serine, threonine, glutamic acid, aspartic acid, glutamine, asparagine, phenylalanine, tyrosine, proline and tryptophan; phenols such as phenol, catechol and hydroquinone; aromatic carboxylic acids such as benzoic acid, 4-hydroxybenzoic acid, protocatechuic acid, phthalic acid, isophthalic acid and terephthalic acid; nucleosides such as inosine and guanosine, nucleotides such as inosinic acid and guanylic acid; unsaturated hydrocarbon compounds such as isobutylene, isoprene and butadiene; and the like.

Of the organic compounds, alcohols, amines, carboxylic acids and phenols are preferable because a known method can be used for the fermentative production and because these organic compounds can be used as resin materials, and aliphatic alcohols having 2 to 10 carbon atoms and aliphatic carboxylic acids having 2 to 10 carbon atoms are more preferable. From the viewpoint of fermentative productivity, ethanol, butanediol and succinic acid are further preferable of the organic compounds.

(Microorganism)

The microorganism used in invention 1-3 is not particularly limited as long as the microorganism is capable of producing organic matter, but the microorganism is preferably selected from the group consisting of coryneform bacteria, colon bacilli, *Anaerobiospirillum* bacteria, *Actinobacillus* bacteria, *Mannheimia* bacteria, *Basfia* bacteria, *Zymomonas* bacteria, *Zymobacter* bacteria, filamentous fungi and yeasts.

Of the microorganisms, at least one selected from the group consisting of coryneform bacteria, colon bacilli, *Anaerobiospirillum* bacteria, *Actinobacillus* bacteria, *Mannheimia* bacteria, *Basfia* bacteria, *Zymobacter* bacteria, filamentous fungi and yeasts is preferable. A coryneform bacterium, a colon *bacillus* or a yeast is more preferable, and a coryneform bacterium is particularly preferable.

The coryneform bacterium is not particularly limited as long as the bacterium is classified as a coryneform bacterium, but examples thereof include bacteria belonging to *Corynebacterium*, bacteria belonging to *Brevibacterium*, bacteria belonging to *Arthrobacter* and the like, preferably bacteria belonging to *Corynebacterium* and *Brevibacterium*, further preferably bacteria classified as *Corynebacterium glutamicum*, *Brevibacterium flavum*, *Brevibacterium ammoniagenes* or *Brevibacterium lactofermentum*.

Particularly preferable specific examples of the coryneform bacteria which can be used in invention 1-3 are *Brevibacterium flavum* MJ-233 (FERM BP-1497) and MJ-233 AB-41 (FERM BP-1498), *Brevibacterium ammoniagenes* ATCC6872, *Corynebacterium glutamicum* ATCC31831, *Brevibacterium lactofermentum* ATCC13869 and the like. In this regard, *Brevibacterium flavum* is sometimes classified as *Corynebacterium glutamicum* (Lielbl W, Ehrmann M, Ludwig W, Schleifer K H, Int J Syst Bacteriol., 1991, Vol. 41, p 255-260), and thus in invention 1, *Brevibacterium flavum* strain MJ-233 and a mutant thereof, strain MJ-233 AB-41, are identical to *Corynebacterium glutamicum* strain MJ-233 and strain MJ-233 AB-41, respectively.

*Brevibacterium flavum* MJ-233 was deposited on Apr. 28, 1975 in Fermentation Research Institute, Agency of Industrial Science and Technology, Ministry of International Trade and Industry (current International Patent Organism Depositary, National Institute of Advanced Industrial Science and Technology) (Central 6, 1-1-1 Higashi, Tsukuba, Ibaraki 305-8566, Japan) with the accession number FERM P-3068 and transferred to an international depositary authority under the Budapest Treaty on May 1, 1981 with the accession number FERM BP-1497.

The colon bacilli which can be used in invention 1-3 are *Escherichia coli* and the like. The *Anaerobiospirillum* bacteria which can be used in invention 1-3 are *Anaerobiospirillum succiniciproducens* and the like.

The *Actinobacillus* bacteria which can be used in invention 1-3 are *Actinobacillus succinogenes* and the like. The *Mannheimia* bacteria which can be used in invention 1-3 are *Mannheimia succiniciproducens* and the like.

The *Basfia* bacteria which can be used in invention 1-3 are *Basfia succiniciproducens* and the like. The *Zymomonas* bacteria which can be used in invention 1-3 are *Zymomonas mobilis* and the like. The *Zymobacter* bacteria which can be used in invention 1-3 are *Zymobacter palmae* and the like.

The filamentous fungi which can be used in invention 1-3 are filamentous fungi of *Aspergillus*, *Penicillium*, *Rhizopus* and the like. The *Aspergillus* fungi are *Aspergillus niger*, *Aspergillus oryzae* and the like, and the *Penicillium* fungi are *Penicillium chrysogenum*, *Penicillium simplicissimum* and the like. The *Rhizopus* fungi are *Rhizopus oryzae* and the like.

The yeasts which can be used in invention 1-3 are yeasts of *Saccharomyces*, *Shizosaccharomyces*, *Candida*, *Pichia*, *Kluyveromyces*, *Yarrowia* and *Zygosaccharomyces*.

The yeasts of *Saccharomyces* are *Saccharomyces cerevisiae*, *Saccharomyces uvarum*, *Saccharomyces bayanus* and the like. The yeasts of Shizosaccharomyces are *Schizosaccharomyces pombe* and the like. The yeasts of *Candida* are *Candida albicans*, *Candida sonorensis*, *Candida glabrata* and the like. The yeasts of *Pichia* are *Pichia pastoris*, *Pichia stipitis* and the like.

The yeasts of *Kluyveromyces* are *Kluyveromyces lactis*, *Kluyveromyces marxianus*, *Kluyveromyces thermotolerans* and the like. The yeasts of *Yarrowia* are *Yarrowia lipolytica* and the like. The yeasts of *Zygosaccharomyces* are *Zygosaccharomyces bailii*, *Zygosaccharomyces rouxii* and the like.

The microorganism is not limited to a wild-type strain but may be any strain of mutants obtained by general mutagenesis such as UV radiation or NTG treatment, recombinant strains induced by genetic engineering such as cell fusion or genetic recombination technique and the like.

The above microorganisms are microorganisms which are originally capable of producing organic matter, but the capability of producing organic matter may be given by breeding.

The means for giving the capability of producing organic matter by breeding is mutagenesis, genetic recombination or the like, and known methods for enhancing the expression of an enzyme gene involved in the biosynthesis pathway of organic matter or decreasing the expression of an enzyme gene involved in the biosynthesis pathway of by-products and the like can be used. When the capability of producing a carboxylic acid such as succinic acid, fumaric acid or malic acid is to be given for example, means for modifying to reduce the lactate dehydrogenase activity and means for enhancing the pyruvate carboxylase activity, which are described below, and the like are used. When the capability of producing an alcohol such as ethanol, butanol or butanediol is to be given, means for modifying to reduce the lactate dehydrogenase activity and means for enhancing the alcohol dehydrogenase activity, which are described below, and the like are used.

The modification method for reducing the lactate dehydrogenase (hereinafter referred to as LDH) activity is not particularly limited, but a strain can be obtained by treating any of the above microorganisms as a parent strain with a mutagen which is generally used for mutagenesis such as N-methyl-N'-nitro-N-nitrosoguanidine (NTG) or nitrous acid and selecting a strain with reduced LDH activity. Also, the LDH activity may be modified using a gene encoding LDH. Specifically, the modification is achieved for example by disrupting an ldh gene on the chromosome or by modifying a regulatory sequence such as a promoter or the Shine-Dalgarno (SD) sequence.

Specific methods for producing a strain with reduced LDH activity are a method by homologous recombination on the chromosome (see JP-A-11-206385 or the like), a method using a sacB gene (Schafer A, Tauch A, Jager W, Kalinowski J, Thierbach G, Puhler A, Gene 1994 Vol. 145(1), p 69-73) and the like.

The modification method for enhancing the pyruvate carboxylase (hereinafter also referred to as PC) activity is not particularly limited, but a strain can be obtained by treating any of the above microorganisms as a parent strain with a mutagen which is generally used for mutagenesis such as N-methyl-N'-nitro-N-nitrosoguanidine (NTG) or nitrous acid and selecting a strain with enhanced PC activity. Also, the PC activity may be modified using a gene encoding PC. Specifically, the modification can be achieved by increasing the copy number of a pc gene, and the copy number can be increased for example using a plasmid or by introducing multiple copies into the chromosome by a known homologous recombination method. The PC activity can be enhanced also by increasing the expression level, for example by introducing a mutation into the promoter of a pc gene on the chromosome or on a plasmid or replacing the promoter with a more potent promoter.

The pc gene used for enhancing the PC activity is not particularly limited as long as the gene encodes a protein having the PC activity, but an example thereof is the gene derived from *Corynebacterium glutamicum*. Moreover, pc genes derived from bacteria apart from coryneform bacteria, other microorganisms, animals or plants can also be used. As the pc genes derived from microorganisms, animals or plants, a gene whose nucleotide sequence has already been determined, a gene encoding a protein having the PC activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

A PC expression vector is provided by inserting a gene encoding PC which has been isolated in the above manner into a known expression vector in an expressible manner. A strain with enhanced PC activity can be obtained through transformation with the expression vector. Alternatively, a strain with enhanced PC activity can be obtained also by inserting DNA encoding PC into the chromosomal DNA of the host microorganism in an expressible manner through homologous recombination or the like. The transformation and the homologous recombination can be conducted according to general methods known to one skilled in the art.

When a PC gene is introduced into the chromosome or a plasmid, an appropriate promoter is inserted into the 5'-upstream region of the gene, and more preferably, a terminator is further inserted into the 3'-downstream region. The promoter and the terminator are not particularly limited as long as the promoter and the terminator are known to function in the microorganism used as the host. The promoter and the terminator of the pc gene itself may be used or replaced with another promoter and another terminator. Vectors, promoters, terminators and the like which can be used in the microorganisms are described in detail for example in *Biseibutsugaku kiso kouza* 8, *Idenshi kougaku*, Kyoritsu Shuppan Co., Ltd. and the like.

When the capability of producing an alcohol is given to the microorganism used in invention 1 by breeding, a microorganism modified to reduce the LDH activity by a method similar to the method for giving the capability of producing a carboxylic acid can be used.

A microorganism modified to enhance the alcohol dehydrogenase (hereinafter also referred to as ADH) can be produced by a method similar to the method for enhancing the PC activity.

The adh gene used for enhancing the ADH activity is not particularly limited as long as the gene encodes a protein having the ADH activity, but examples thereof are the adhB gene derived from *Zymomonas mobilis* and the adhE2 gene derived from *Clostridium acetobutylicum*. Moreover, adh genes derived from bacteria apart from the above species, other microorganisms, animals or plants can also be used. As the adh genes derived from microorganisms, animals or plants, a gene whose nucleotide sequence has already been determined, a gene encoding a protein having the ADH activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

The microorganism used in invention 1 may be a microorganism obtained through a combination of two or more types of modification for giving the capability of producing organic matter. When two or more types of modification are introduced, the order thereof may be any order.

The microorganism used in invention 1-3 may be a microorganism capable of producing organic matter and capable of utilizing a pentose and is preferably a microorganism capable of utilizing a pentose. In invention 1, the "capability of utilizing a pentose" means that the microorganism can use a pentose as a carbon source and can multiply or produce organic matter.

The pentose that the microorganism uses as a carbon source is not particularly limited as long as the pentose can be used as a carbon source. Specific examples thereof are aldopentoses such as xylose, arabinose, ribose and lyxose, ketopentoses such as ribulose and xylulose and the like. Of these pentoses, aldopentoses are preferable, and xylose and arabinose, which are contained in hemicellulose-based biomass used as a non-edible material, are more preferable. Xylose, which is contained in hemicellulose-based biomass in a large amount, is particularly preferable.

Here, the microorganism capable of utilizing a pentose may be a microorganism which is originally capable of utilizing a pentose or a microorganism to which the capability of utilizing a pentose has been given by breeding.

The means for giving the capability of utilizing a pentose by breeding is genetic recombination or the like, and a known method such as the introduction of an enzyme gene involved in the pentose metabolic pathway can be used. When the capability of utilizing xylose is to be given for example, a method for introducing a xylose isomerase gene and a method for introducing a xylose reductase gene and a xylitol dehydrogenase gene, which are described below, and the like are used. When the capability of utilizing arabinose is to be given, a method for introducing an arabinose isomerase gene, a ribulokinase gene and a ribulose-5-phosphate epimerase gene, which is described below, and the like are used.

As specific examples of how the capability of utilizing a pentose is given by breeding, an example of the modification to give the capability of utilizing xylose and an example of the modification to give the capability of utilizing arabinose are explained.

A microorganism to which the capability of utilizing xylose has been given can be obtained by introducing a gene encoding a protein having the xylose isomerase (hereinafter also referred to as XylA) activity into any of the above microorganisms as a parent strain.

Here, the "XylA activity" means the activity of catalyzing the reaction in which xylose is isomerized into xylulose (EC: 5.3.1.5). That the XylA activity has been given or enhanced can be confirmed by measuring the XylA activity by a known method such as the method of Gao et al. (Gao Q, Zhang M, McMillan J D, Kompala D S, Appl. Biochem. Biotechnol., 2002, Vol. 98(100), p 341-55).

Specific methods for producing a strain in which the XylA activity has been given or enhanced are the introduction of a xylA gene using a plasmid, the introduction of a xylA gene into the chromosome by a known homologous recombination method and the like.

The xylA gene used for giving or enhancing the XylA activity is not particularly limited as long as the gene encodes a protein having the XylA activity, but an example thereof is the gene derived from *Escherichia coli*.

Moreover, xylA genes derived from bacteria apart from colon bacilli, other microorganisms, animals or plants can also be used. As the xylA genes derived from microorganisms, animals or plants, a gene whose nucleotide sequence has already been determined, a gene encoding a protein having the XylA activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

A XylA expression vector is provided by inserting a gene encoding XylA which has been isolated in the above manner into a known expression vector in an expressible manner. A strain in which the XylA activity has been given or enhanced can be obtained through transformation with the expression vector. Alternatively, a strain in which the XylA activity has been given or enhanced can be obtained also by inserting DNA encoding XylA into the chromosomal DNA of the host microorganism in an expressible manner through homologous recombination or the like. The transformation and the homologous recombination can be conducted according to general methods known to one skilled in the art.

When a XylA gene is introduced into the chromosome or a plasmid, an appropriate promoter is inserted into the 5'-upstream region of the gene, and more preferably, a terminator is further inserted into the 3'-downstream region. The promoter and the terminator are not particularly limited as long as the promoter and the terminator are known to function in the microorganism used as the host. The promoter and the terminator of the xylA gene itself may be used or replaced with another promoter and another terminator. Vectors, promoters, terminators and the like which can be used in the microorganisms are described in detail for example in *Biseibutsugaku kiso kouza* 8, *Idenshi kougaku*, Kyoritsu Shuppan Co., Ltd. and the like.

The microorganism to which the capability of utilizing xylose has been given may be a microorganism which has been modified to give or enhance the xylulokinase (hereinafter also referred to as XylB) activity as well as to give or enhance the XylA activity.

Here, the "XylB activity" means the activity of catalyzing the reaction in which xylulose is phosphorylated into xylulose 5-phosphate (EC: 2.7.1.17). That the XylB activity has been given or enhanced can be confirmed by measuring the XylB activity by a known method such as the method of Eliasson et al. (Eliasson A, Boles E, Johansson B, Otensterberg M, Thevelein J M, Spencer-Martins I, Juhnke H, Hahn-Hatengerdal B, Appl. Microbiol. Biotechnol., 2000, Vol. 53, p 376-82).

A strain in which the XylB activity has been given or enhanced can be produced by a method similar to the method for giving or enhancing the XylA activity.

The xylB gene used for giving or enhancing the XylB activity is not particularly limited as long as the gene encodes a protein having the XylB activity, but examples thereof are the genes derived from *Escherichia coli* and *Corynebacterium glutamicum*.

Moreover, xylB genes derived from bacteria apart from the species, other microorganisms, animals or plants can also be used. As the xylB genes derived from microorganisms, animals or plants, a gene whose nucleotide sequence has already been determined, a gene encoding a protein having the XylB activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

When the XylA activity and the XylB activity are given or enhanced, the xylA gene and the xylB gene to be introduced may be at the same locus or may be at different loci. An example in which the two genes are at the same locus is an operon formed by the genes linked to each other or the like.

A microorganism to which the capability of utilizing xylose has been given can be obtained also by introducing a gene encoding a protein having the xylose reductase (hereinafter also referred to as XR) activity and a gene encoding a protein having the xylitol dehydrogenase (hereinafter also referred to as XDH) activity into any of the above microorganisms as a parent strain.

Here, the "XR activity" means the activity of catalyzing the reaction in which xylose is reduced into xylitol (EC: 1.1.1.21). That the XR activity has been given or enhanced can be confirmed by measuring the XR activity by a known method such as the method of Sasaki et al. (Sasaki M, Jojima T, Inui M, Yukawa H, Appl Microbiol Biotechnol., 2010, Vol. 86(4), p 1057-66).

A strain in which the XR activity has been given or enhanced can be produced by a method similar to the method for giving or enhancing the XylA activity. The xr gene used for giving or enhancing the XR activity is not particularly limited as long as the gene encodes a protein having the XR activity, but an example thereof is the XYL1 gene derived from *Pichia stipitis*.

Moreover, xr genes derived from microorganisms apart from the species, animals or plants can also be used. As the xr genes derived from microorganisms, animals or plants, a gene whose nucleotide sequence has already been determined, a gene encoding a protein having the XR activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

Next, the "XDH activity" means the activity of catalyzing the reaction in which xylitol is dehydrogenated into xylulose (EC: 1.1.1.9). That the XDH activity has been given or enhanced can be confirmed by measuring the XDH activity by a known method such as the method of Rizzi et al. (Rizzi M, Harwart K, Erlemann P, Bui-Thahn N A, Dellweg H, J Ferment Bioeng., 1989, Vol. 67, p 20-24).

A strain in which the XDH activity has been given or enhanced can be produced by a method similar to the method for giving or enhancing the XylA activity. The xdh gene used for giving or enhancing the XDH activity is not particularly limited as long as the gene encodes a protein having the XDH activity, but an example thereof is the XYL2 gene derived from *Pichia stipitis*.

Moreover, xdh genes derived from microorganisms apart from the species, animals or plants can also be used. As the xdh genes derived from microorganisms, animals or plants, a gene whose nucleotide sequence has already been determined, a gene encoding a protein having the XDH activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

The microorganism to which the capability of utilizing xylose has been given may be a microorganism which has been modified to give or enhance the XylB activity as well as to give or enhance the XDH activity and the XR activity. The XylB activity is given or enhanced as described above.

A microorganism to which the capability of utilizing arabinose has been given can be obtained by introducing a gene encoding a protein having the arabinose isomerase (hereinafter also referred to as AraA) activity, a gene encoding a protein having the ribulokinase (hereinafter also referred to as AraB) activity and a gene encoding a protein having the ribulose-5-phosphate epimerase (hereinafter also referred to as AraD) activity into any of the above microorganisms as a parent strain.

Here, the "AraA activity" means the activity of catalyzing the reaction in which arabinose is isomerized into ribulose (EC: 5.3.1.4). That the AraA activity has been given or enhanced can be confirmed by measuring the AraA activity by a known method such as the method of Patrick et al. (Patrick J W, Lee N, J. Biol. Chem., 1968, Vol. 243, p 4312-19).

A strain in which the AraA activity has been given or enhanced can be produced by a method similar to the method for giving or enhancing the XylA activity. The araA gene used for giving or enhancing the AraA activity is not particularly limited as long as the gene encodes a protein having the AraA activity, but examples thereof are the gene derived from *Escherichia coli* and *Corynebacterium glutamicum*.

Moreover, araA genes derived from bacteria apart from the species, other microorganisms, animals or plants can also be used. As the araA genes derived from microorganisms, animals or plants, a gene whose nucleotide sequence has already been determined, a gene encoding a protein having the AraA activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

Next, the "AraB activity" means the activity of catalyzing the reaction in which ribulose is phosphorylated into ribulose 5-phosphate (EC: 2.7.1.16). That the AraB activity has been given or enhanced can be confirmed by measuring the AraB activity by a known method such as the method of Lee et al. (Lee N, Englesberg E, Proc. Natl. Acad. Sci., 1962, Vol. 48, p 335-48).

A strain in which the AraB activity has been given or enhanced can be produced by a method similar to the method for giving or enhancing the XylA activity. The araB gene used for giving or enhancing the AraB activity is not particularly limited as long as the gene encodes a protein having the AraB activity, but examples thereof are the genes derived from *Escherichia coli* and *Corynebacterium glutamicum*.

Moreover, araB genes derived from bacteria apart from the species, other microorganisms, animals or plants can also be used. As the araB genes derived from microorganisms, animals or plants, a gene whose nucleotide sequence has already been determined, a gene encoding a protein having the AraB activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

Furthermore, the "AraD activity" means the activity of catalyzing the reaction in which ribulose 5-phosphate is isomerized into xylulose 5-phosphate (EC: 5.1.3.4). That the AraD activity has been given or enhanced can be confirmed by measuring the AraD activity by a known method such as the method of Deanda et al. (Deanda K, Zhang M, Eddy C, Picataggio S, Appl Environ Microbiol., 1996, Vol. 62(12), p 4465-70).

A strain in which the AraD activity has been given or enhanced can be produced by a method similar to the method for giving or enhancing the XylA activity. The araD gene used for giving or enhancing the AraD activity is not particularly limited as long as the gene encodes a protein having the AraD activity, but examples thereof are the genes derived from *Escherichia coli* and *Corynebacterium glutamicum*.

Moreover, araD genes derived from bacteria apart from the species, other microorganisms, animals or plants can also be used. As the araD genes derived from microorganisms, animals or plants, a gene whose nucleotide sequence has already been determined, a gene encoding a protein having the AraD activity which is isolated from the chromosome of a microorganism, an animal, a plant or the like based on the homology or the like and which is then sequenced and the like can be used. Also, after the nucleotide sequence has been determined, a gene synthesized according to the sequence can also be used. Such a gene can be obtained by amplifying a region including the promoter and the ORF through the hybridization method and the PCR method.

When the AraA activity, the AraB activity and the AraD activity are given or enhanced, the araA gene, the araB gene and the araD gene to be introduced may be at the same locus or may be at different loci. An example in which two or three of the genes are at the same locus is an operon formed by the genes linked to each other or the like.

The microorganism used in invention 1-3 may be a bacterium obtained through a combination of two or more types of modification for giving the capability of utilizing a pentose. When two or more types of modification are introduced, the order thereof may be any order.

Moreover, the microorganism used in invention 1-3 may be a microorganism obtained through a combination of the modification for giving the capability of producing organic matter and the modification for giving the capability of utilizing a pentose. When two or more types of modification are introduced, the order thereof may be any order.

(Organic-Matter Production Step)

Invention 1-3 includes a step of obtaining an organic compound by causing a microorganism capable of producing organic matter to act on an organic raw material containing the treated saccharide solution of invention 1-2 in an aqueous medium described below (hereinafter sometimes referred to as an organic-matter production step). In particular, it is preferable to generate an organic compound by causing the above microorganism to act on an organic raw material containing the treated saccharide solution and recover the organic compound. The kinds of organic compound which can be produced and preferable examples of the organic compound are as described above. In this regard, the "aqueous medium" means liquid which contains water, an aqueous solution containing water as a main component and gel (agar) or the like and which contains an organic raw material containing a saccharide solution, a microorganism capable of producing organic matter, an adduct of a reducing agent and a carbonyl compound except for the saccharide contained in the organic raw material and a component necessary for culturing the microorganism, and liquid in which undissolved liquid or solid is dispersed is also included.

When the microorganism is used in invention 1-3, the microorganism cultured by slant culture on a solid medium such as an agar medium may be used directly, but the microorganism which has been cultured in a liquid medium in advance may be used according to the need. That is, the microorganism may be multiplied in advance and then caused to produce an organic compound. The microorganism can be multiplied in advance through seed culture or main culture described below, and the organic raw material used here may be the treated saccharide solution or another organic raw material.

The organic compound may be produced by reacting a microorganism cultured through seed culture or main culture with an organic raw material containing the treated saccharide solution while the microorganism is multiplied in an aqueous medium. The organic compound may be produced also by reacting microorganism cells which have been multiplied through seed culture or main culture in advance with an organic raw material containing the treated saccharide solution in an aqueous medium containing the organic raw material.

As the microorganism used in invention 1-3, a treated microorganism can also be used as well as the microorganisms. Examples of the treated microorganism include immobilized cells obtained by immobilizing cells of a microorganism with acrylamide, carrageenan or the like, homogenized cells, supernatant obtained by centrifuging the homogenized cells, a fraction obtained by partially purifying the supernatant with ammonium sulfate treatment or the like and other treated products.

An organic raw material containing the treated saccharide solution is used in invention 1-3, and another organic raw material may be added according to the need. The organic raw material other than the treated saccharide solution used in the method for producing an organic compound is not particularly limited as long as the organic raw material is a carbon source which the microorganism can assimilate to generate an organic compound. In general, a carbohydrate such as galactose, lactose, glucose, fructose, sucrose, starch or cellulose; or fermentable sugar such as a polyalcohol e.g. glycerol, mannitol, xylitol or ribitol is used. Of these materials, glucose, sucrose or fructose is preferable, and glucose or sucrose is particularly preferable.

A saccharified solution of starch, molasses or the like containing the fermentable sugar can also be used as the organic raw material other than the treated saccharide solution, and specifically, a saccharide solution obtained by squeezing a plant such as sugar cane, sugar beet or sugar maple is preferable.

One of the organic raw materials may be added alone, or a combination of the organic raw materials may be added.

The concentration of the organic raw material for use is not particularly limited, but a concentration which is as high as possible but which does not inhibit the generation of the organic compound is advantageous. The concentration based on the aqueous medium is generally 50 g/L or more, preferably 100 g/L or more and is generally 300 g/L or less, preferably 200 g/L or less. The organic raw material may be further added as the amount of the organic raw material decreases with the progress of the reaction.

(Aqueous Medium)

The "aqueous medium" used in invention 1-3 is not particularly limited but is preferably an aqueous solution containing a nitrogen source, an inorganic salt or the like. Here, the nitrogen source is not particularly limited as long as the microorganism used in invention 1-3 can assimilate the nitrogen source to generate an organic compound. Specific examples include organic and inorganic nitrogen compounds such as ammonium salts, nitrates, urea, soybean hydrolysate, casein decomposition product, peptone, yeast extract, meat extract and corn steep liquor. As the inorganic salt, phosphates, sulfates and salts of metals such as magnesium, potassium, manganese, iron and zinc are used. Also, a growth promoter such as vitamins e.g. biotin, thiamine, pantothenic acid, inositol and nicotinic acid, nucleotides and amino acids is added according to the need. To prevent foaming during the reaction, an appropriate amount of a commercially available defoaming agent is preferably added to the aqueous medium.

The aqueous medium preferably contains at least one selected from carbonate ion, bicarbonate ion and carbon dioxide gas for example in addition to the organic raw material, the nitrogen source, the inorganic salt and the like. Carbonate ion or bicarbonate ion is supplied from magnesium carbonate, sodium carbonate, sodium bicarbonate, potassium carbonate, potassium bicarbonate or the like, which can be used also as a neutralizer, but can be supplied also from carbonic acid, bicarbonic acid, a salt thereof or carbon dioxide gas according to the need. Specific examples of the salt of carbonic acid or bicarbonic acid are magnesium carbonate, ammonium carbonate, sodium carbonate, potassium carbonate, ammonium bicarbonate, sodium bicarbonate, potassium bicarbonate and the like.

The concentration of carbonate ion or bicarbonate ion in the aqueous medium is generally 1 mM or more, preferably 2 mM or more, further preferably 3 mM or more and is generally 500 mM or less, preferably 300 mM or less, further preferably 200 mM or less. When carbon dioxide gas is contained, it is preferable that carbon dioxide gas is contained in an amount of generally 50 mg or more, preferably 100 mg or more, further preferably 150 mg or more per 1 L aqueous medium, and it is preferable that carbon dioxide gas is contained in an amount of generally 25 g or less, preferably 15 g or less, further preferably 10 g or less per 1 L aqueous medium.

The pH of the aqueous medium is preferably adjusted in a range in which the activity of the microorganism used is exhibited most effectively, in accordance with the kind of the microorganism. Specifically, when a coryneform bacterium is used, it is preferable that the pH of the aqueous medium is generally 5.5 or more, preferably 6 or more, more preferably 6.6 or more, further preferably 7.1 or more and is generally 10 or less, preferably 9.5 or less, more preferably 9.0 or less.

When the organic compound produced is an acidic substance, the pH of the aqueous medium can be adjusted by adding sodium carbonate, sodium bicarbonate, potassium carbonate, potassium bicarbonate, magnesium carbonate, ammonium carbonate, ammonium bicarbonate, sodium hydroxide, calcium hydroxide, magnesium hydroxide, ammonia (ammonium hydroxide), a mixture thereof or the like. When the organic compound produced is a basic substance, the pH of the aqueous medium can be adjusted by adding an inorganic acid such as hydrochloric acid, sulfuric acid or phosphoric acid, an organic acid such as acetic acid, a mixture thereof or the like or by supplying carbon dioxide gas.

(Reaction Conditions of Organic-Matter Production Step)

The amount of the microorganism cells used in invention 1-3 is not particularly limited, but the wet cell mass is generally 1 g/L or more, preferably 10 g/L or more, more preferably 20 g/L or more and is generally 700 g/L or less, preferably 500 g/L or less, further preferably 400 g/L or less.

The reaction period of the organic-matter production step in invention 1-3 is not particularly limited but is generally one hour or longer, preferably three hours or longer and is generally 168 hours or shorter, preferably 72 hours or shorter.

The reaction temperature of the organic-matter production step in invention 1-3 may be the same temperature as the optimum temperature for the growth of the microorganism used. However, a temperature which is higher than the optimum temperature for the growth is advantageous, and the temperature is generally 2° C. or more, preferably 7° C. or more, more preferably 15° C. or more, further preferably 20° C. or more higher than the optimum temperature for the growth. Specifically, in the case of a coryneform bacterium, the temperature is generally 35° C. or higher, preferably 37° C. or higher, further preferably 39° C. or higher and is generally 45° C. or lower, preferably 43° C. or lower, further preferably 41° C. or lower. It is not necessary to always keep the temperature in the range of 35° C. to 45° C. throughout the reaction for producing the organic compound, but it is desirable to keep the temperature in the range in 50% or more, preferably 80% or more of the total reaction period.

The organic-matter production step of invention 1-3 may be conducted with aeration or stirring, but the step is preferably conducted in an anaerobic atmosphere without aeration and without supplying oxygen. The anaerobic atmosphere here can be achieved by a method in which the reaction is conducted without aeration in a closed container, a method in which the reaction is conducted while supplying an inert gas such as nitrogen gas, a method in which an inert gas containing carbon dioxide gas is supplied and the like.

The organic-matter production step of invention 1-3 is not especially limited but can be applied to any of batch reaction, semi-batch reaction and continuous reaction.

(Other Steps)

In invention 1-3, an organic compound can be generated and accumulated in the aqueous medium by the organic-matter production step. A step of recovering the organic compound accumulated by the organic-matter production step from the aqueous medium according to a general method may be further included. Specifically, when the organic compound accumulated is a carboxylic acid such as succinic acid, fumaric acid or malic acid for example, the organic compound can be recovered by removing solid materials such as cells by centrifugation, filtration or the like and then desalting using an ion exchange resin or the like.

In invention 1-3, a step of purifying the product obtained by the recovery step may be further included. Specifically, the solution recovered from the aqueous medium can be purified by crystallization or column chromatography, and a carboxylic acid can be thus obtained. When the organic compound accumulated is an alcohol such as ethanol, butanol or butanediol, the alcohol can be purified by removing solid materials such as cells by centrifugation, filtration or the like, then concentrating the solution by distillation or the like and dehydrating the solution using a membrane.

<Invention 1-4: Culture Method of Microorganism>

In the culture method of invention 1-4, a microorganism capable of producing organic matter is cultured using an organic raw material containing the treated saccharide solution of invention 1-2 as a carbon source. The microorganism obtained by the culture method of invention 1-4 can be then caused to act on an organic raw material to generate an organic compound, which can be then recovered. The treated saccharide solution may be used as the organic raw material here, or another organic raw material may be contained in the treated saccharide solution. The kinds of organic compound which can be produced and preferable examples of the organic compound are as described above.

In the culture method of invention 1-4, the microorganism may be cultured on a solid medium, such as an agar medium, containing the treated saccharide solution or cultured in a liquid medium containing the treated saccharide solution. Through seed culture or main culture described below, the microorganism which is subjected to the reaction for producing an organic compound can be multiplied.

(Seed Culture)

The seed culture is for preparing cells of the microorganism which are subjected to main culture. The culture medium used for seed culture may be a general culture medium used for culturing a microorganism but is preferably a culture medium containing a nitrogen source, an inorganic salt or the like. Here, the nitrogen source is not particularly limited as long as the microorganism can assimilate the nitrogen source and multiply. Specific examples include organic and inorganic nitrogen compounds such as ammonium salts, nitrates, urea, soybean hydrolysate, casein decomposition product, peptone, yeast extract, meat extract and corn steep liquor. As the inorganic salt, phosphates, sulfates and salts of metals such as magnesium, potassium, manganese, iron and zinc are used. Also, a growth promoter such as vitamins e.g. biotin, thiamine, pantothenic acid, inositol and nicotinic acid, nucleotides and amino acids is added according to the need. Moreover, according to the need, a treated saccharide solution may be added as a carbon source to the culture medium, or an organic raw material such as glucose may be added.

The seed culture is preferably conducted at a general optimum temperature for the growth. The general optimum temperature for the growth means the temperature at which the growth rate is the highest under the conditions used for the production of the organic compound. The specific culture temperature is generally 25° C. to 40° C., preferably 30° C. to 37° C. In the case of a coryneform bacterium, the culture temperature is generally 25° C. to 35° C., more preferably 28° C. to 33° C., particularly preferably about 30° C.

The seed culture is preferably conducted at general optimum pH for the growth. The general optimum pH for the growth means the pH at which the growth rate is the highest under the conditions used for the production of the organic compound. The specific pH for the culture is generally 4 to 10, preferably 6 to 8. In the case of a coryneform bacterium, the pH is generally 6 to 9, preferably 6.5 to 8.5.

The culture period of the seed culture is not especially limited as long as a certain amount of cells can be obtained during the period but the culture period is generally six hours or longer and 96 hours or shorter. During the seed culture, oxygen is preferably supplied by aeration, stirring or the like.

The cells after the seed culture can be used for main culture described below. However, the seed culture may be skipped, and cells cultured by slant culture on a solid medium such as an agar medium may be used directly in the main culture. Also, the seed culture may be repeated several times according to the need.

(Main Culture)

The main culture is for preparing cells of the microorganism which are subjected to the reaction for producing an organic compound described below, and the main purpose is to increase the amount of the cells. When the seed culture is conducted, the main culture is conducted using the cells obtained by the seed culture.

The culture medium used for main culture may be a general culture medium used for culturing a microorganism but is preferably a culture medium containing a nitrogen source, an inorganic salt or the like. Here, the nitrogen source is not particularly limited as long as the microorganism can assimilate the nitrogen source and multiply. Specific examples include organic and inorganic nitrogen compounds such as ammonium salts, nitrates, urea, soybean hydrolysate, casein decomposition product, peptone, yeast extract, meat extract and corn steep liquor. As the inorganic salt, phosphates, sulfates and salts of metals such as magnesium, potassium, manganese, iron and zinc are used. Also, a growth promoter such as vitamins e.g. biotin, thiamine, pantothenic acid, inositol and nicotinic acid, nucleotides and amino acids is added according to the need. Moreover, to prevent foaming during the culture, an appropriate amount of a commercially available defoaming agent is preferably added to the culture medium.

For the main culture, an organic raw material containing the treated saccharide solution is used as a carbon source. Another organic raw material may be added according to the need. The organic raw material other than the treated saccharide solution used in the main culture is not particularly limited as long as the microorganism can assimilate the organic raw material and multiply. In general, a carbohydrate such as galactose, lactose, glucose, fructose, sucrose, saccharose, starch or cellulose; or fermentable sugar such as a polyalcohol e.g. glycerol, mannitol, xylitol or ribitol is used. Of these materials, glucose, sucrose or fructose is preferable, and glucose or sucrose is particularly preferable.

One of the organic raw materials may be added alone, or an optional combination of two or more thereof may be added.

The concentration of the organic raw material for use is not particularly limited, and addition at a concentration which does not inhibit the multiplication is advantageous. The organic raw material can be used at a concentration in the range of generally 1 to 100 g/L, preferably 5 to 50 g/L based on the culture liquid. The organic raw material may be further added as the amount of the organic raw material decreases with the multiplication.

The main culture is preferably conducted at a general optimum temperature for the growth. The specific culture temperature is generally 25° C. to 40° C., preferably 30° C. to 37° C. In the case of a coryneform bacterium, the culture temperature is generally 25° C. to 35° C., more preferably 28° C. to 33° C., particularly preferably about 30° C.

The main culture is preferably conducted at general optimum pH for the growth. The specific pH for the culture is generally 4 to 10, preferably 6 to 8. In the case of a coryneform bacterium, the pH is generally 6 to 9, preferably 6.5 to 8.5.

The culture period of the main culture is not especially limited as long as a certain amount of cells can be obtained during the period but the culture period is generally six hours or longer and 96 hours or shorter. During the main culture, oxygen is preferably supplied by aeration, stirring or the like.

For the main culture, the culture method described in JP-A-2008-259451, in which depletion and supply of the carbon source are repeated alternately in a short time, can be also used as a method for preparing cells which are more suitable for the production of an organic compound.

The cells after the main culture can be used for the reaction for producing an organic compound. The culture liquid may be used directly, or the cells recovered by centrifugation, membrane separation or the like may be used.

<<Invention 2>>

The method for treating a saccharide solution, the method for producing a treated saccharide solution, the reduced saccharide solution, the method for producing an organic compound and the culture method according to invention 2 are described in detail below.

<Invention 2-1: Treatment Method of Saccharide Solution>

Invention 2-1 of invention 2 is characterized by subjecting a saccharide solution to reduction using an ionic compound containing an anion containing one or more kinds of sulfur having an oxidation number selected from −2, +2, +3 and +4 and ammonium ion as a reducing agent and reducing a carbonyl compound except for the saccharide contained in the saccharide solution.

The saccharide solution of invention 2-1 and the "saccharide solution" used in invention 2-2, invention 2-3 and invention 2-4 (inventions 2-1 to 2-4 are sometimes called "invention 2" together) described below mean an aqueous solution containing a saccharide. In invention 2-1, the ionic compound containing an anion containing one or more kinds of sulfur having an oxidation number selected from −2, +2, +3 and +4 and ammonium ion is sometimes referred to as "the reducing agent of invention 2". The explanation is made below in order from the saccharide contained in the saccharide solution.

(Saccharide)

The saccharide contained in the saccharide solution used in invention 2 is not particularly limited, and so-called saccharides in general can be used. Specifically, those in (Saccharide) explained in the item <Invention 1-1> are used, and the preferable range is also the same.

(Origin and Production Method of Saccharide Solution)

The method for producing the saccharide solution used in invention 2 is not particularly limited, but examples thereof include a production method in which one or more of the saccharides are dissolved in water and a production method in which a raw material containing the saccharide as a component (hereinafter sometimes referred to as "a saccharide raw material") is degraded into the constituent unit saccharide. Specifically, the origins and the methods in (Origin and Production Method of Saccharide Solution) explained in the item <Invention 1-1> are used, and the preferable ranges are also the same.

(Carbonyl Compound Except for Saccharide)

The saccharide solution used in invention 2 generally contains a carbonyl compound which is generated during the step of producing the saccharide solution and during the storage in addition to the saccharide. Specific examples of the carbonyl compound are those in (Carbonyl Compound except for Saccharide) explained in the item <Invention 1-1>, and the preferable range is also the same.

The inventors have found that the carbonyl compound except for the saccharide reduces/decreases the production amount, the accumulation amount and the production rate of a useful compound in the step of producing the useful compound from a saccharide solution by fermentation. Hereinafter, a substance having the effect is called "a fermentation inhibitor" in general. The inventors have also found that a saccharide solution containing the fermentation inhibitor decreases the multiplication amount and the multiplication rate in the step of culturing a microorganism and causes coloration of the product in the step of producing an organic compound through a chemical conversion process due to the high reactivity of the carbonyl compound.

(Reduction)

In invention 2-1, the carbonyl compound except for the saccharide contained in the saccharide solution is reduced using the reducing agent of invention 2. As a result, the carbonyl compound is converted into a substance which inhibits fermentation less, and thus the amount thereof can be decreased. The "reduction" in invention 2-1 means treatment for converting the carbonyl compound except for the saccharide contained in the saccharide solution into a substance which has been reacted with the reducing agent of invention 2 (hereinafter sometimes referred to as "a reduction product").

It is presumed that the reduction product is generated because the carbonyl group of the carbonyl compound except for the saccharide contained in the saccharide solution reacts with the reducing agent. It is presumed that when an aldehyde compound is subjected to reduction using a sulfite or a hyposulfite as the reducing agent for example, the aldehyde compound is converted into α-hydroxysulfonate. The carbonyl compound is preferably at least one selected from aldehyde compounds and ketone compounds. This is because these compounds often have the property of highly inhibiting fermentation in invention 2-3 and invention 2-4 described below.

By subjecting the saccharide solution to the reduction, the inhibitory effect on the fermentative production of an organic compound can be reduced, and the fermentation process of the saccharide solution can be conducted without decreasing the multiplication rate and the multiplication amount in the culture step of a microorganism. Also in the chemical conversion process, since the carbonyl group, which is highly reactive, is converted, the coloration of the product or the like can be prevented.

(Reducing Agent)

The reduction in invention 2-1 is conducted in the presence of the reducing agent of invention 2. The reducing agent used in invention 2 is an ionic compound. The ionic compound contains an anion containing one or more kinds of sulfur having an oxidation number selected from −2, +2, +3 and +4. Also, the ionic compound contains ammonium ion as the cation thereof.

By using the ionic compound as the reducing agent, the amount of the carbonyl compound contained in the saccharide solution, preferably a water-soluble aldehyde compound, can be decreased, and the yield of the organic compound in the fermentative production process described below can be increased. Also, because no metal salt is used, no reducing-agent-derived metal is contained in the later fermentation process, purification process of the fermentation liquid and the like, and the burden imposed by the removal of a metal salt can be reduced.

The anion of the ionic compound is an anion containing one or more kinds of sulfur having an oxidation number selected from −2, +2, +3 and +4.

Here, the oxidation number of sulfur is a value indicating the charges that the sulfur atom would have if the electrons in the reducing agent were assigned to the atoms by certain methods. The certain methods are (a) to (e) below. The oxidation number of sulfur contained in the reducing agent can be determined unambiguously using the methods. (a) The oxidation number of a monatomic ion in an ionic compound is equal to the number of charges. (b) The oxidation number of an atom in a simple substance is considered 0. (c) With respect to a covalent compound, the oxidation number of an atom is the number of charges which would remain on the atom if each shared electron pair were assigned to the atom having higher electronegativity. (d) The number is divided equally when two or more identical elements are contained in a compound. (e) When the oxidation number is determined, the oxidation number of hydrogen is regarded as +1 and the oxidation number of oxygen is regarded as −2.

Specifically, anions containing sulfur having an oxidation number of −2 are sulfide ion and the like. Anions containing sulfur having an oxidation number of +2 are thiosulfate ion and the like. Anions containing sulfur having an oxidation number of +3 are hyposulfite ion and the like. Anions containing sulfur having an oxidation number of +4 are sulfite ion, hydrogen sulfite ion and the like.

More specifically, at least one anion selected from sulfite ion, hydrogen sulfite ion, hyposulfite ion, thiosulfate ion and sulfide ion is preferable, and sulfite ion and hyposulfite ion are more preferable because these ions are easily obtained and easily handled.

Using an ionic compound containing such an anion, the carbonyl compound content of the saccharide solution can be decreased.

The ionic compound used in invention 2 is not particularly limited as long as the ionic compound contains the anion and ammonium ion, and specifically, the ionic compound is a diammonium salt, a monoammonium salt or the like.

Specifically, the ionic compound is a sulfite such as ammonium sulfite, a hydrogen sulfite such as ammonium hydrogen sulfite, a hyposulfite such as ammonium hyposulfite, a thiosulfate such as ammonium thiosulfate or a sulfide such as ammonium sulfide. Ammonium sulfite and ammonium hyposulfite are preferable because these compounds are easily obtained and easily handled.

As long as the effects of invention 2 are not impaired, one of the reducing agents may be used, or two or more of the reducing agents may be used. Also, the ratio of the reducing agents used is not limited.

(Conditions of Reduction)

The conditions of the reduction in invention 2-1 are not particularly limited as long as the amount of the carbonyl compound except for the saccharide contained in the saccharide solution is reduced.

The saccharide contained in the saccharide solution also has an aldehyde group and the like, and these groups react with the reducing agent of invention 2, like the carbonyl compound. That is, also when a reaction product of the saccharide and the reducing agent is generated, the conditions of the reduction are not limited as long as no problem arises in the step of producing a useful compound by fermentation and the step of culturing a microorganism, which are described below. Accordingly, it is preferable to select selective reaction conditions under which the amount of the carbonyl compound except for the saccharide can be reduced and under which the saccharide such as glucose or xylose does not easily react with the reducing agent of invention 2.

The treatment temperature of the reduction in invention 2-1 is not particularly limited but is generally 20° C. or higher and 100° C. or lower, preferably 80° C. or lower. By conducting the reduction at a temperature within the range, the degradation of the reducing agent and the reduction product can be inhibited, and the amount of the carbonyl compound except for the saccharide, which is a fermentation inhibitor, can be reduced without causing the saccharide to react with the reducing agent.

The amount of the reducing agent used in the reduction in invention 2-1 is determined by the conditions such as the concentration of the fermentation inhibitor in the saccharide solution, the kind of the reducing agent used, the reaction temperature, the reaction style and the amount of the saccharide solution to be treated and by the desired results of the reaction such as the efficiency of the removal of the fermentation inhibitor, inhibition of the reaction between the saccharide and the reducing agent and decrease in the amount of the unreacted reducing agent. Thus, the amount of the reducing agent is not particularly limited.

The ratio by mole of the reducing agent to the amount of the carbonyl compound except for the saccharide contained in the saccharide solution is generally 0.05 or more, preferably 0.2 or more and is generally 2.0 or less, preferably 1.5 or less.

The treatment period of the reduction in invention 2-1 is determined by the conditions such as the amount and the concentration of the carbonyl compound in the saccharide solution, the kind of the reducing agent used, the reaction temperature, the reaction style and the amount of the saccharide solution to be treated and by the desired results of the reaction such as the efficiency of the removal of the fermentation inhibitor and inhibition of the reaction between the saccharide and the reducing agent. Thus, the treatment period is not particularly limited.

The decrease in the carbonyl compound content may not advance sufficiently when the reaction period is short, while the amount of the reaction product of the saccharide and the reducing agent increases for example when the reaction period is long, which both cause problems.

A solvent can be used in the reduction in invention 2-1. The kind thereof is not particularly limited, but water is generally used. An organic solvent may be used as a cosolvent. However, an organic solvent mixed in the aqueous phase may inhibit fermentation and requires a step of separating the organic solvent before the fermentative production or the step of culturing a microorganism. Thus, it is desirable that the saccharide solution in the form of aqueous solution is directly subjected to the reduction.

<Invention 2-2: Reduced Saccharide Solution>

Because the amount of the carbonyl compound except for the saccharide contained in the saccharide solution is reduced by the reduction in invention 2-1, the concentration of the carbonyl compound in the saccharide solution obtained is generally lower than the concentration in the original saccharide solution. In this regard, the saccharide solution which has been subjected to the reduction is sometimes referred to as "a reduced saccharide solution" below.

By reacting the carbonyl compound with the reducing agent of invention 2, the efficiencies of the multiplication of a microorganism and of the fermentative production of a useful compound can be improved in the fermentation process described below.

The reduced saccharide solution of invention 2-2 may contain the reaction product of the carbonyl compound and the reducing agent, and specifically, when the carbonyl compound is an aldehyde compound, the reduced saccharide solution may contain corresponding α-hydroxysulfonate or the like.

The reduced saccharide solution of invention 2-2 may be further treated appropriately with an ion exchange resin, active carbon or a synthetic resin or by a method such as hydrogenation according to the need.

<Invention 2-3: Production Method of Organic Compound>

Various organic compounds can be produced by causing a microorganism capable of producing organic matter to act on the reduced saccharide solution of invention 2-2.

(Microorganism Capable of Producing Organic Matter)

The microorganism used in invention 2-3 is not particularly limited as long as the microorganism is capable of producing organic matter.

The "microorganism capable of producing organic matter" in invention 2-3 means a microorganism that can generate and accumulate organic matter in a culture medium when the microorganism is cultured in the culture medium.

(Organic Compound)

The organic compound that the microorganism produces is not limited as long as the microorganism can generate and accumulate the organic compound in a culture medium. Specifically, those in (Organic Compound) explained in the item <Invention 1-3> are used, and the preferable range is also the same.

(Microorganism)

The microorganism used in invention 2-3 is not particularly limited as long as the microorganism is capable of producing organic matter. Specifically, those in (Microorganism) explained in the item <Invention 1-3> are used, and the preferable range is also the same.

(Organic-Matter Production Step)

Invention 2-3 includes a step of obtaining an organic compound by causing a microorganism capable of producing organic matter to act on an organic raw material containing the reduced saccharide solution of invention 2-2 in a reaction solution (hereinafter sometimes referred to as an organic-matter production step). In particular, it is preferable to generate an organic compound by causing the above microorganism to act on an organic raw material containing the reduced saccharide solution and recover the organic compound. The kinds of organic compound which can be produced and preferable examples of the organic compound are as described above.

When the microorganism is used in invention 2-3, the microorganism cultured by slant culture on a solid medium such as an agar medium may be used directly, but the microorganism which has been cultured in a liquid medium in advance may be used according to the need. That is, the microorganism may be multiplied in advance and then caused to produce an organic compound. The microorganism can be multiplied in advance through seed culture or main culture as described below, and the organic raw material used here may be the reduced saccharide solution or another organic raw material.

The organic compound may be produced by reacting a microorganism cultured through seed culture or main culture with an organic raw material containing the reduced saccharide solution while the microorganism is multiplied in a reaction solution. The organic compound may be produced also by reacting microorganism cells which have been multiplied through seed culture or main culture in advance with an organic raw material containing the reduced saccharide solution in a reaction solution containing the organic raw material.

As the microorganism used in invention 2-3, a treated microorganism can also be used as well as the microorganisms. Examples of the treated microorganism include immobilized cells obtained by immobilizing cells of a microorganism with acrylamide, carrageenan or the like, homogenized cells, supernatant obtained by centrifuging the homogenized cells, a fraction obtained by partially purifying the supernatant with ammonium sulfate treatment or the like and other treated products.

An organic raw material containing the reduced saccharide solution is used in invention 2-3, and another organic raw material may be added according to the need. The organic raw material other than the reduced saccharide solution used in the method for producing an organic compound is not particularly limited as long as the organic raw material is a carbon source which the microorganism can assimilate to generate an organic compound. In general, a carbohydrate such as galactose, lactose, glucose, fructose, sucrose, starch or cellulose; or fermentable sugar such as a polyalcohol e.g. glycerol, mannitol, xylitol or ribitol is used. Of these materials, glucose, sucrose or fructose is preferable, and glucose or sucrose is particularly preferable.

A saccharified solution of starch, molasses or the like containing the fermentable sugar can also be used, and specifically, a saccharide solution obtained by squeezing a plant such as sugar cane, sugar beet or sugar maple is preferable.

One of the organic raw materials may be added alone, or a combination of the organic raw materials may be added.

The concentration of the organic raw material for use is not particularly limited, but a concentration which is as high as possible but which does not inhibit the generation of the organic compound is advantageous. The concentration based on the reaction solution is generally 50 g/L or more, preferably 100 g/L or more and is generally 300 g/L or less, preferably 200 g/L or less. The organic raw material may be further added as the amount of the organic raw material decreases with the progress of the reaction.

(Reaction Solution)

The reaction solution used in invention 2-3 is not particularly limited and may be a culture medium for culturing the microorganism or a buffer such as phosphate buffer for example. However, the reaction solution is preferably an aqueous solution containing a nitrogen source, an inorganic salt or the like. Here, the nitrogen source is not particularly limited as long as the microorganism used in invention 2-3 can assimilate the nitrogen source to generate an organic compound. Specifically, those in (Aqueous Medium) explained in the item <Invention 1-3> are used, and the preferable range is also the same.

The reaction solution preferably contains at least one selected from carbonate ion, bicarbonate ion and carbon dioxide gas for example in addition to the organic raw material, the nitrogen source, the inorganic salt and the like for example. Specifically, those in (Aqueous Medium) explained in the item <Invention 1-3> are used, and the preferable range is also the same. The concentration of carbonate ion or bicarbonate ion and the pH of the reaction solution are also preferably in the same ranges as those in (Aqueous Medium) explained in the item <Invention 1-3>. The subject matters explained in the item (Aqueous Medium) can be applied here by reading "aqueous medium" as "reaction solution".

(Reaction Conditions of Organic-Matter Production Step)

The amount of the microorganism cells, the reaction temperature, the oxygen supply conditions and the reaction style used in invention 2-3 are not particularly limited, but the ranges in (Reaction Conditions of Organic-Matter Production Step) explained in the item <Invention 1-3> are preferable.

(Other Steps)

In invention 2-3, an organic compound can be generated and accumulated in the reaction solution by the organic-matter production step. Thus, the steps in (Other Steps) explained in the item <Invention 1-3> may be further included.

<Invention 2-4: Culture Method of Microorganism>

In the culture method of invention 2-4, a microorganism capable of producing organic matter is cultured using an organic raw material containing the reduced saccharide solution of invention 2-2 as a carbon source. The microorganism obtained by the culture method of invention 2-4 can be then caused to act on an organic raw material to generate an organic compound, which can be then recovered. The reduced saccharide solution may be used as the organic raw material here, or another organic raw material may be contained in the reduced saccharide solution. The kinds of organic compound which can be produced and preferable examples of the organic compound are as described above.

In the culture method of invention 2-4, the microorganism may be cultured on a solid medium, such as an agar medium, containing the reduced saccharide solution or cultured in a liquid medium containing the reduced saccharide solution. The microorganism can be cultured by the method in (Seed Culture) explained in the item <Invention 1-4>, and the same range is preferable.

(Main Culture)

The main culture is for preparing cells of the microorganism which are subjected to the reaction for producing an organic compound described below, and the main purpose is to increase the amount of the cells. When the seed culture is conducted, the main culture is conducted using the cells obtained by the seed culture.

The culture medium used for the main culture is preferably in the same range as that in (Main Culture) explained in the item <Invention 1-4>.

For the main culture, an organic raw material containing the reduced saccharide solution is used as a carbon source. Another organic raw material may be added according to the need. The organic raw material other than the reduced saccharide solution used in the main culture and the concentration thereof are the same as those in (Main Culture) explained in the item <Invention 1-4>, and the same ranges are preferable.

The culture period of the main culture, the oxygen supply conditions, the method for preparing cells and the application to the reaction for producing an organic compound are not particularly limited, but the ranges in (Main Culture) explained in the item <Invention 1-4> are preferable.

EXAMPLES

The invention is explained in further detail below using Examples, but the invention should not be limited by the Examples.

<Analysis Conditions>

(Liquid Chromatograph (LC) Analysis)

The amounts of the components contained in the saccharide solutions of Production Examples, Examples and Comparative Examples below were determined by liquid chromatograph (LC) analysis using the absolute calibration method. The conditions of the analysis are as follows.

(LC Measurement Condition 1: conditions of analysis of saccharides, formic acid, glycolaldehyde (GAL), ethanol and succinic acid)

Column: ULTRON PS-80H 8.0 ID×300 mm (manufactured by Shinwa Chemical Industries, Ltd.)

Column temperature: 40° C. or 60° C.

Eluent: 0.11 mass % perchloric acid solution, 1.0 mL/min

Detection method: UV (210 nm) or RI

Injection amount: 10 μL (LC Measurement Condition 2: conditions of analysis of furfural and hydroxymethylfurfural)

Column: Develosil C30, length 100 mm×4.6 mm, particle diameter 3 (manufactured by Nomura Chemical Co., Ltd.)

Eluent: solution A aqueous 0.054 mass % perchloric acid solution solution B acetonitrile gradient analysis from solution A/solution B=95/5 (volume/volume) to solution B 100 volume % in 20 minutes Flow rate: 1.0 mL/min Detection method: UV (210 nm)

Injection amount: 5 μL.

(LC Measurement Condition 3: conditions of analysis of saccharides contained in culture supernatant)

Column: COSMOSIL Sugar—D Packed Column 4.6 mm I.D.×250 mm (manufactured by Nacalai Tesque, Inc.)

Column temperature: 30° C.

Eluent: 75 vol % acetonitrile, 1.0 mL/min

Detection method: RI

Injection amount: 10 μL

Examples 1-1 to 1-10 and Comparative Examples 1-1 to 1-5

Production Example 1-1

Bagasse was used as a non-edible material. First, sulfuric acid and water were added to and mixed with bagasse, and a bagasse mixture was obtained. The amount of sulfuric acid added was 2 mass % based on the dry mass of bagasse, and the amount of water added was adjusted in such a manner that the water content became 60 mass % based on the total mass of the bagasse mixture. Next, the bagasse mixture was mixed and stirred for 20 minutes with a drum mixer (manufactured by Sugiyama Heavy Industrial Co., Ltd.) and then taken out, and a mixture treated with dilute sulfuric acid was thus obtained. The mixture treated with dilute sulfuric acid was subjected to steaming treatment at 180° C. for 15 minutes in a hydrolysis machine (manufactured by Yasujima Co., Ltd) by introducing steam into the machine. The water content of the steamed material obtained was 64.6 mass %. Into a saccharification machine, 200 g/L of the steamed material in terms of dry mass was charged, and the pH was adjusted at 6.0 by adding an aqueous 10N-NaOH solution. CTec2 (manufactured by Novozymes A/S) in an amount equivalent to 15 FPU was added thereto as a saccharification enzyme, and the material was hydrolyzed at a temperature of 50° C. while stirring the solution at a stirring speed of 200 rpm for 72 hours. Then, undegraded cellulose and lignin were separated and removed by centrifugation (10000 g, 10 minutes), and a saccharified solution of bagasse was thus produced. The composition of the saccharified solution of bagasse obtained is shown in Table 1.

The saccharified solution of bagasse was centrifuged (8000×g, 10 minutes) to remove solid materials contained in the saccharified solution of bagasse. Subsequently, the saccharified solution of bagasse was filtered using filter paper of a retained particle diameter of 1 μm, and thus a filtrate 1 was produced.

TABLE 1

| Saccharified solution of bagasse | Saccharide concentration (g/L) | Glu 98 | Xyl 25 | Suc 12 | Fru 3 | | | |
|---|---|---|---|---|---|---|---|---|
| | Fermentation inhibitor concentration (g/L) | FRL 2.0 | HMF 0.8 | HBA 0.06 | SYA 0.03 | VAN 0.04 | Acetic acid 7.1 | Formic acid 2.3 |

\* In the table, Glu represents glucose, Xyl represents xylose, Suc represents sucrose, and Fru represents fructose.
\* In the table, FRL represents furfural, HMF represents hydroxymethylfurfural, HBA represents hydroxybenzaldehyde, SYA represents syringaldehyde, and VAN represents vanillin.

Production Example 1-2

The pH of the filtrate 1 obtained in Production Example 1-1 was adjusted at 8 using an aqueous 48 mass % NaOH solution, and the filtrate 1 was heated at 121° C. for 20 minutes, thereby producing a saccharified solution 1-1.

The saccharified solution 1-1 was analyzed by LC under the LC measurement conditions 1 and 2. As a result, the glucose content was 7.4 mass %, the fructose content was 0.7 mass %, the xylose content was 3.6 mass %, the furfural content was 524 ppm, and the hydroxymethylfurfural content was 443 ppm.

Example 1-1

To the saccharified solution 1-1 prepared by heating in the same manner as in Production Example 1-2, 0.6 mass % of sodium sulfite based on the total mass of glucose, fructose and xylose that the saccharified solution 1-1 contained was added at 40° C.

Subsequently, the saccharified solution 1-1 was stirred at the same temperature of 40° C. for an hour, and a treated saccharide solution was thus obtained (hereinafter referred to as "a treated saccharide solution 1-1"). The treated saccharide solution 1-1 was analyzed by LC under the same conditions as those for the saccharified solution 1-1 to determine the amounts of the components contained. As a result, the glucose content was 7.4 mass %, the fructose content was 0.7 mass %, the xylose content was 3.6 mass %, the furfural content was 513 ppm, and the hydroxymethylfurfural content was 426 ppm. The results of the measurement are shown in Table 2.

Example 1-2

A treated saccharide solution 1-2 was obtained by treating the saccharified solution 1-1 in the same manner as in Example 1-1 except that the reducing agent used was changed to sodium hydrogen sulfite. The treated saccharide solution 1-2 was analyzed by LC under the same conditions as those in Example 1-1. As a result, the glucose content was 7.5 mass %, the fructose content was 0.7 mass %, the xylose content was 3.4 mass %, the furfural content was 474 ppm, and the hydroxymethylfurfural content was 431 ppm. The results of the measurement are shown in Table 2.

Example 1-3

A treated saccharide solution 1-3 was obtained by treating the saccharified solution 1-1 in the same manner as in Example 1-2 except that the amount of sodium hydrogen sulfite used was changed to 0.4 mass % based on the total mass of glucose, fructose and xylose. The treated saccharide solution 1-3 was analyzed by LC under the same conditions as those in Example 1-1. As a result, the glucose content was 7.8 mass %, the fructose content was 0.6 mass %, the xylose content was 3.3 mass %, the furfural content was 486 ppm, and the hydroxymethylfurfural content was 434 ppm. The results of the measurement are shown in Table 2.

Example 1-4

A treated saccharide solution 1-4 was obtained by treating the saccharified solution 1-1 in the same manner as in Example 1-3 except that the period of the treatment with the reducing agent was changed to two hours. The treated saccharide solution 1-4 was analyzed by LC under the same conditions as those in Example 1-1. As a result, the glucose content was 7.6 mass %, the fructose content was 0.7 mass %, the xylose content was 3.4 mass %, the furfural content was 533 ppm, and the hydroxymethylfurfural content was 457 ppm. The results of the measurement are shown in Table 2.

Example 1-5

A treated saccharide solution 1-5 was obtained by treating the saccharified solution 1-1 in the same manner as in Example 1-1 except that the reducing agent used was changed to an aqueous 50 mass % ammonium sulfite solution and that the amount of the aqueous 50 mass % ammonium sulfite solution was changed to 1.1 mass % based on the total mass of glucose, fructose and xylose. The treated saccharide solution 1-5 was analyzed by LC under the same conditions as those in Example 1-1. As a result, the glucose content was 7.6 mass %, the fructose content was 0.7 mass %, the xylose content was 3.4 mass %, the furfural content was 489 ppm, and the hydroxymethylfurfural content was 445 ppm. The results are shown in Table 2.

Comparative Example 1-1

To the filtrate 1 prepared in Production Example 1-1, 0.6 mass % of sodium sulfite based on the total mass of glucose, fructose and xylose that the filtrate 1 contained was added at 40° C., and the mixture was stirred at the same temperature of 40° C. for an hour and then cooled to 25° C. Then, the pH was adjusted at 8 using an aqueous 48 mass % NaOH solution, and the mixture was heated at 121° C. for 20 minutes, thereby producing a treated saccharide solution 1-6. The treated saccharide solution 1-6 was analyzed by LC under the same conditions as those in Example 1-1. As a result, the glucose content was 7.4 mass %, the fructose content was 0.6 mass %, the xylose content was 3.6 mass %, the furfural content was 487 ppm, and the hydroxymethylfurfural content was 441 ppm. The results of the measurement are shown in Table 2.

Comparative Example 1-2

The filtrate 1 was treated in the same manner as in Comparative Example 1-1 except that the reducing agent used was changed to sodium hydrogen sulfite. Then, the pH was adjusted at 8 using an aqueous 48 mass % NaOH solution, and the mixture was heated at 121° C. for 20 minutes, thereby producing a treated saccharide solution 1-7. The treated saccharide solution 1-7 was analyzed by LC under the same conditions as those in Example 1-1. As a result, the glucose content was 7.12 mass %, the fructose content was 0.75 mass %, the xylose content was 3.31 mass %, the furfural content was 482 ppm, and the hydroxymethylfurfural content was 445 ppm. The results of the measurement are shown in Table 2.

genase-disrupted strain (*Brevibacterium flavum* MJ233/ΔLDH), then modifying the strain into pyruvate carboxylase-enhanced strain (*Brevibacterium flavum* MJ233/PC-4/ΔLDH) and further introducing a xylose isomerase gene and a xylulokinase gene.

Of the production methods, the method for producing *Brevibacterium flavum* strain MJ233/PC-4/ΔLDH from *Brevibacterium flavum* strain MJ233 was conducted according to the method described in JP-A-2015-29471.

TABLE 2

| | Order of treatment (treated saccharide solution) | Conditions of heat treatment | Conditions of reduction ||||| Concentrations of components in saccharide solution |||||
|---|---|---|---|---|---|---|---|---|---|---|---|
| | | | Reducing agent | Amount (mass %) | Treatment temperature (° C.) | Treatment period (hr) | Glu (mass %) | Fru (mass %) | Xyl (mass %) | FRL (ppm) | HMF (ppm) |
| Example 1-1 | heat treatment → reduction (treated saccharide solution 1-1) | 121° C. 20 min | Na$_2$SO$_3$ | 0.6 | 40 | 1 | 7.4 | 0.7 | 3.6 | 513 | 426 |
| Example 1-2 | heat treatment → reduction (treated saccharide solution 1-2) | | NaHSO$_3$ | 0.6 | 40 | 1 | 7.5 | 0.7 | 3.4 | 474 | 431 |
| Example 1-3 | heat treatment → reduction (treated saccharide solution 1-3) | | NaHSO$_3$ | 0.4 | 40 | 1 | 7.8 | 0.6 | 3.3 | 486 | 434 |
| Example 1-4 | heat treatment → reduction (treated saccharide solution 1-4) | | NaHSO$_3$ | 0.4 | 40 | 2 | 7.6 | 0.7 | 3.4 | 533 | 457 |
| Example 1-5 | heat treatment → reduction (treated saccharide solution 1-5) | | (NH$_4$)$_2$SO$_3$ | 0.6 | 40 | 1 | 7.7 | 0.7 | 3.4 | 489 | 445 |
| Production Example 1-2 | heat treatment (saccharified solution 1-1) | | — | — | — | — | 7.4 | 0.7 | 3.6 | 524 | 443 |
| Comparative Example 1-1 | heat treatment → reduction (treated saccharide solution 1-6) | | Na$_2$SO$_3$ | 0.6 | 40 | 1 | 7.4 | 0.6 | 3.6 | 487 | 411 |
| Comparative Example 1-2 | heat treatment → reduction (treated saccharide solution 1-7) | | NaHSO$_3$ | 0.6 | 40 | 1 | 7.1 | 0.8 | 3.3 | 482 | 445 |

\* In the table, Glu represents glucose, Fru represents fructose, and Xyl represents xylose.
\* In the table, FRL represents furfural, and HMF represents hydroxymethylfurfural.

Production Example 1-3

Production of Xylose Isomerase Gene- and Xylulokinase Gene-Introduced Strain

As the microorganism used in invention 1-3 of the invention, a microorganism producing succinic acid was produced and used.

As the microorganism producing succinic acid, *Brevibacterium flavum* MJ233/XylAB/PC-4/ΔLDH obtained by modifying *Brevibacterium flavum* strain MJ233 was used.

The microorganism is a strain obtained by modifying *Brevibacterium flavum* strain MJ233 into a lactate dehydrogenase-disrupted strain (*Brevibacterium flavum* MJ233/ΔLDH), then modifying the strain into pyruvate carboxylase-enhanced strain.

The method for producing *Brevibacterium flavum* MJ233/XylAB/PC-4/ΔLDH from *Brevibacterium flavum* MJ233/PC-4/ΔLDH is described specifically below.

(A) Extraction of *Escherichia coli* Genome DNA

*Escherichia coli* strain JM109 was cultured in 10 mL of a TB medium [Terrific Broth 47 g/L and Glycerol 5 g/L] to the late logarithmic growth phase, and the cells were collected. The cells obtained were suspended in 0.15 mL of a buffer [20 mM Tris-HCl pH8.0, 10 mM NaCl and 1 mM EDTA.2Na] containing lysozyme at a concentration of 10 mg/mL. Next, proteinase K was added at a final concentration of 100 μg/mL to the suspension, and the mixture was incubated at 37° C. for an hour. Furthermore, sodium dodecyl sulfate was added at a final concentration of 0.5 mass %, and the mixture was incubated at 50° C. for six hours to cause bacteriolysis. An equivalent amount of a phenol/chloroform solution was added to the lysate, and the mixture was shaken gently at room temperature for 10 minutes. Then, the entire amount of the mixture was centrifuged (5000×g, 20 minutes, 10 to 12° C.), and the supernatant fraction was collected. Sodium acetate was added to the fraction in such a manner that the concentration thereof became 0.3 M. Then, twice the amount of ethanol was added and mixed, and the precipitates recovered by centrifugation (15000×g, two minutes) were washed with 70 volume % ethanol and air-dried. Five milliliters of a TE buffer [10 mM Tris-HCl pH7.5 and 1 mM EDTA.2Na] were added to the DNA obtained, and the mixture was left still at 4° C. overnight and used as the template DNA for the following PCR.

(B) Cloning of Xylose Isomerase-Xylulokinase Gene Operon

The xylAB operon of *Escherichia coli* strain JM109 was obtained by PCR using the DNA prepared in (A) above as the template and using synthetic DNA fragments, 5'-AAAGGATCCATCACCCGCGGCATTACCTG-3' (SEQ ID NO: 1) and 5'-TTTGGGCCCGTCGACTGAGA-TATATAGATGTGAATTATCC-3'(SEQ ID NO: 2), which were designed based on the sequences around the operon of *Escherichia coli* strain K12-MG1655 whose whole genome sequence had been reported (GenBank Accession No. U00096).

One microliter of the template DNA, 0.5 μL of Pfx DNA polymerase (Invitrogen), the included buffer at 1× concentration, the primers each at 0.4 μM, 1 mM MgSO$_4$ and 0.25 μM dNTPs were mixed, and the total amount was adjusted to 50 μL. With respect to the conditions of the reaction temperatures, 35 cycles each consisting of 15 seconds at 94° C., 30 seconds at 55° C. and three minutes at 68° C. were conducted using a DNA thermal cycler, PTC-200 (MJ Research). In this regard, the period of incubation at 94° C. in the first cycle was two minutes, and the period of incubation at 68° C. in the final cycle was five minutes.

The amplified fragments were confirmed by separating the fragments by electrophoresis using 0.9 mass % agarose gel and then visualizing the fragments by ethidium bromide staining, and fragments of about 3.0 kb were detected. The DNA fragments of the xylAB operon obtained were purified using ChargeSwitch PCR Clean-Up Kit (Invitrogen) and then digested with restriction enzymes BamHI and ApaI. The DNA fragments of about 2.9 kb generated by the digestion were detected by separating the fragments by electrophoresis using 0.9 mass % agarose gel and then visualizing the fragments by ethidium bromide staining, and the fragments were recovered from the gel using Zymoclean Gel DNA Recovery Kit (Zymo Research). The DNA fragments were mixed with DNA prepared by digesting pTZ4 with restriction enzymes BamHI and ApaI, and the DNA fragments were ligated to the DNA using DNA Ligation Kit ver. 2 (Takara Bio Inc.). *Escherichia coli* (strain DH5α) was transformed with the plasmid DNA obtained and spread onto an LB agar medium containing 50 μg/mL kanamycin. A clone which grew on the culture medium was liquid-cultured in a TB medium [Terrific Broth 47 g/L and Glycerol 5 g/L] (containing 50 μg/mL kanamycin), and then the plasmid DNA was prepared using QIAprep Spin Miniprep Kit (QIAGEN). The plasmid DNA thus obtained was digested with restriction enzymes BamHI and ApaI. As a result, an inserted fragment of about 2.9 kb was confirmed, and the plasmid was named pXylAB1.

(C) Construction of Plasmid for Introducing Xylose Isomerase-Xylulokinase Gene Operon In order to introduce the XylAB operon derived from *Escherichia coli* into the ldh gene-knockout site on the chromosome of *Brevibacterium flavum* strain MJ233/PC-4/ ΔLDH (JP-A-2015-29471), an ldh gene was cloned. The ldh gene of *Brevibacterium flavum* strain MJ233 was obtained by PCR using the DNA prepared in (A) of Production Example 1-3 as the template and using synthetic DNA fragments, 5'-CGAGGGGTCGAGGATTCTGGGGAGGA-TCGAGTGGATTC-3' (SEQ ID NO: 3) and 5'-TCTA-GAGTCGAGGATGGTGA CCATGATGCAGGATGGAG-3' (SEQ ID NO: 4), which were designed based on the sequences around the gene of *Corynebacterium glutamicum* strain ATCC13032 whose whole genome sequence had been reported (GenBank Accession No. BA000036).

One microliter of the template DNA, 0.5 μL of Pfx DNA polymerase (Invitrogen), the included buffer at 1× concentration, the primers each at 0.4 μM, 1 mM MgSO$_4$ and 0.25 μM dNTPs were mixed, and the total amount was adjusted to 50 μL. With respect to the conditions of the reaction temperatures, 35 cycles each consisting of 15 seconds at 94° C., 30 seconds at 55° C. and two minutes at 68° C. were conducted using a DNA thermal cycler, PTC-200 (MJ Research). In this regard, the period of incubation at 94° C. in the first cycle was two minutes, and the period of incubation at 68° C. in the final cycle was five minutes.

The amplified fragments were confirmed by separating the fragments by electrophoresis using 0.9 mass % agarose gel and then visualizing the fragments by ethidium bromide staining, and fragments of about 2.1 kb were detected. The DNA fragments of the ldh gene obtained were purified using ChargeSwitch PCR Clean-Up Kit (Invitrogen) and then ligated to the XbaI site of pKMB1 (JP-A-2005-95169) using In-Fusion Cloning Kit (Takara Bio Inc.), and *Escherichia coli* strain DH5α was transformed with the plasmid DNA obtained. The recombinant *Escherichia coli* thus obtained was spread onto an LB agar medium containing 25 μg/mL kanamycin and 25 μg/mL X-Gal.

A clone which formed a white colony on the culture medium was liquid-cultured in a TB medium [Terrific Broth 47 g/L and Glycerol 5 g/L] (containing 25 μg/mL kanamycin), and then the plasmid DNA was prepared using QIAprep Spin Miniprep Kit (QIAGEN). The plasmid DNA thus obtained was digested with restriction enzymes XhoI and BglI. As a result, an inserted fragment of about 2.2 kb was confirmed, and the plasmid was named pKB-LDH2.

The XylAB operon linked to a TZ4 promoter which was derived from *Brevibacterium flavum* strain MJ233 and which would be highly expressed due to the structure was obtained by PCR using the plasmid pXylAB1 as the template and using synthetic DNA fragments described in 5'-GTACCTGCAGGATGAGCGGGCT-3' (SEQ ID NO: 5) and 5'-CACCCGGTCAGGCAGGGGATAAC-3' (SEQ ID NO: 6).

One microliter of the template DNA, 0.5 μL of Prime-STAR Max DNA polymerase (Invitrogen), the included buffer at 1× concentration and the primers each at 0.4 μM were mixed, and the total amount was adjusted to 50 μL. With respect to the conditions of the reaction temperatures, 30 cycles each consisting of 15 seconds at 94° C., 20 seconds at 55° C. and 45 seconds at 72° C. were conducted using a DNA thermal cycler, PTC-200 (MJ Research). In this regard, the period of incubation at 94° C. in the first cycle was two minutes.

The amplified fragments were confirmed by separating the fragments by electrophoresis using 0.7 mass % agarose gel and then visualizing the fragments by ethidium bromide staining, and fragments of about 3.2 kb were detected. The 5'-termini of the DNA fragments of the XylAB operon linked to the TZ4 promoter obtained were phosphorylated with T4 Polynucleotide Kinase (Takara Bio Inc.), and the DNA fragments were ligated to the EcoRV site of the pKB-LDH2 using DNA Ligation Kit ver. 2 (Takara Bio Inc.). *Escherichia coli* strain DH5α was transformed with the plasmid DNA obtained. The recombinant *Escherichia coli* thus obtained was spread onto an LB agar medium containing 25 µg/mL kanamycin.

A clone which grew on the culture medium was liquid-cultured in a TB medium [Terrific Broth 47 g/L and Glycerol 5 g/L] (containing 25 µg/mL kanamycin), and then the plasmid DNA was prepared using QIAprep Spin Miniprep Kit (QIAGEN). The nucleotide sequence of the fragment inserted to the plasmid DNA thus obtained was determined using BigDye Terminator v3 Cycle Sequencing Kit and a DNA sequencer, 377XL (Applied Biosystems). As a result, the nucleotide sequence (the XylAB operon) obtained was completely identical to the genome sequence of *Escherichia coli* strain K12-MG1655, and it was confirmed that no mutation had been introduced to the XylAB operon. This was named pXylAB3

(D) Production of Xylose Isomerase-Xylulokinase Gene Operon-Introduced Strain

The plasmid DNA used for the transformation of *Brevibacterium flavum* strain MJ233/PC-4/ΔLDH was re-prepared from *Escherichia coli* strain JM110 transformed with the pXylAB3 by the calcium chloride method (Journal of Molecular Biology, 1970, 53, 159).

*Brevibacterium flavum* strain MJ233/PC-4/ΔLDH was transformed by the electric pulse method (Res. Microbiol., 1993, 144, p 181-5), and the transformant obtained was spread onto an LBG agar medium [10 g of tripton, 5 g of yeast extract, 5 g of NaCl, 20 g of glucose and 15 g of agar dissolved in 1 L of distilled water] containing 25 µg/mL kanamycin.

Because the pXylAB3 is a plasmid which is not replicable in the cells of *Brevibacterium flavum* strain MJ233, it is expected that in a strain which grew on the culture medium, the ldh gene of the plasmid and the gene on the genome of *Brevibacterium flavum* strain MJ233 had been exchanged by homologous recombination and the plasmid-derived kanamycin resistance gene and sacB gene had been inserted to the genome.

Next, the homologous recombinant strains were liquid-cultured in an LBG medium containing 25 µg/mL kanamycin. The culture liquid in an amount equivalent to about 1,000,000 cells was spread onto an LBG medium containing 10 mass % sucrose. As a result, several dozen strains which were believed to be unsusceptible to sucrose because the sacB gene had been removed by second homologous recombination were obtained.

The strains thus obtained included strains in which the pXylAB3-derived XylAB operon linked to the TZ4 promoter had been inserted into the ldh gene-knockout site and strains having a sequence returned to that of the parent strain. Whether the XylAB operon linked to the TZ4 promoter had been inserted or not can be easily confirmed by subjecting the cells obtained by culturing in an LBG medium directly to PCR reaction and detecting the XylAB operon linked to the TZ4 promoter. When a clone to which the XylAB operon linked to the TZ4 promoter has been inserted is analyzed using primers for amplifying the TZ4 promoter and the XylAB operon by PCR, 5'-AATCAG-GAAGTGGGATCGAAAATG-3' (SEQ ID NO: 7) and 5'-CCGCCAACTAGACACCAAAGATTC-3' (SEQ ID NO: 8), DNA fragments of 4,196 by should be observed. Strains which became unsusceptible to sucrose were analyzed by the method, and as a result, a strain to which the XylAB operon linked to the TZ4 promoter had been inserted was selected and named *Brevibacterium flavum* MJ233/XylAB/PC-4/ΔLDH.

Example 1-6

Evaluation of Fermentative Production of Treated Saccharide Solution (A) Seed Culture A thousand milliliters of a culture medium having the composition [4 g of urea, 14 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate pentahydrate, 200 µg of D-biotin, 200 µg of thiamine hydrochloride, 1 g of yeast extract and 1 g of casamino acid dissolved in 1,000 mL of distilled water] (hereinafter referred to as the medium (A)) were heated at 121° C. for 20 minutes and cooled to room temperature. Then, 15 mL of the medium was put into a 200-mL Erlenmeyer flask, and 600 µL of an aqueous 50 mass % glucose solution which had been sterilized in advance was added. *Brevibacterium flavum* strain MJ233/XylAB/PC-4/ΔLDH produced in (D) of Production Example 1-3 was seeded and shake-cultured at 30° C. for 5.2 hours.

(B) Main Culture

To a 500-mL Erlenmeyer flask, 100 mL of the medium A was put, and 4 mL of an aqueous 50 mass % glucose solution which had been sterilized in advance was added. Then, the culture liquid obtained by the seed culture in the medium (A) was seeded in such a manner that the O.D. (660 nm) became 0.02, and the cells were shake-cultured at 30° C. for 22.4 hours.

(C) Reaction for Producing Succinic Acid

Cells were collected from the culture liquid obtained by the main culture of (B) above by centrifugation (5000×g, seven minutes) and suspended in a cell-suspending solution [320 mg of magnesium sulfate heptahydrate, 13 mg of ferrous sulfate heptahydrate, 13 mg of manganese sulfate pentahydrate, 410 mg of phosphoric acid (85 mass %) and 540 mg of potassium hydroxide (48 mass %) dissolved in 1000 mL of distilled water] in such a manner that the O.D. (660 nm) became 60, thereby preparing a cell solution. Subsequently, 56 g of the treated saccharide solution 1-1 produced in Example 1-1, 9 g of distilled water, 1 mL of the cell-suspending solution, 133 mg of an aqueous D-biotin solution (100 mg/L) and 133 mg of an aqueous thiamine hydrochloride solution (100 mg/L) were mixed to produce a substrate solution. To the substrate solution, 960 mg of ammonium hydrogen carbonate and the cell solution were added, and reaction was conducted in an anaerobic atmosphere at 40° C. In this regard, the pH was maintained at 7.3 by adding a neutralizer [97 g of ammonia water (28 mass %) and 32 g of ammonium hydrogen carbonate dissolved in 250 mL of distilled water]. The culture supernatant was analyzed by LC under the LC measurement condition 1. As a result, after 19.1 hours, the succinic acid concentration was 36.9 g/L, the glucose concentration was 0.0 g/L, and the xylose concentration was 15.2 g/L. After 24.4 hours, the succinic acid concentration was 39.1 g/L, the glucose concentration was 0.0 g/L, and the xylose concentration was 13.3 g/L. The results are shown in Table 3.

Comparative Example 1-3

Comparative Example 1-3 was conducted in the same manner as in Example 1-6 except that a substrate solution was produced by mixing 56 g of the saccharified solution 1-1 produced in Production Example 1-2, 9 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 19.1 hours, the succinic acid concentration was 27.2 g/L, the glucose concentration was 16.0 g/L, and the xylose concentration was 15.9 g/L. After 24.4 hours, the succinic acid concentration was 30.4 g/L, the glucose concentration was 11.6 g/L, and the xylose concentration was 14.5 g/L.

Comparative Example 1-4

Comparative Example 1-4 was conducted in the same manner as in Example 1-6 except that a substrate solution was produced by mixing 56 g of the treated saccharide solution 1-6 produced in Comparative Example 1-1, 9 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 19.1 hours, the succinic acid concentration was 29.1 g/L, the glucose concentration was 13.8 g/L, and the xylose concentration was 15.9 g/L. After 24.4 hours, the succinic acid concentration was 32.6 g/L, the glucose concentration was 9.3 g/L, and the xylose concentration was 14.8 g/L. The results are shown in Table 3.

TABLE 3

| | Treatment method of saccharide solution (saccharide solution used) | Period (hr) | Succinic acid concentration (g/L) | Glucose concentration (g/L) | Xylose concentration (g/L) |
|---|---|---|---|---|---|
| Example 1-6 | heat treatment → reduction (treated saccharide solution 1-1) | 19.1<br>24.4 | 36.9<br>39.1 | 0.0<br>0.0 | 15.2<br>13.3 |
| Comparative Example 1-3 | heat treatment (saccharified solution 1-1) | 19.1<br>24.4 | 27.2<br>30.4 | 16.0<br>11.6 | 15.9<br>14.5 |
| Comparative Example 1-4 | reduction → heat treatment (treated saccharide solution 1-6) | 19.1<br>24.4 | 29.1<br>32.6 | 13.8<br>9.3 | 15.9<br>14.8 |

From Table 3, with the saccharide solution of Example 1-6, after 19.1 hours, the succinic acid concentration increased by 36% compared to that of Comparative Example 1-3, and the succinic acid concentration increased by 27% compared to that of Comparative Example 1-4. After 24.4 hours, the succinic acid concentration increased by 29% compared to that of Comparative Example 1-3, and the succinic acid concentration increased by 20% compared to that of Comparative Example 1-4.

From the above results, it has been elucidated that by reacting a reducing agent with a saccharide solution after heating the saccharide solution, the inhibition of the fermentation is reduced in degree, and the production rate of an organic compound increases. The effects cannot be obtained when the saccharide solution is heated after being reacted with the reducing agent.

Example 1-7

Example 1-7 was conducted in the same manner as in Example 1-6 except that a substrate solution was produced by mixing 56 g of the treated saccharide solution 1-2 produced in Example 1-2, 9 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 18.9 hours, the succinic acid concentration was 32.0 g/L, the glucose concentration was 8.3 g/L, and the xylose concentration was 14.9 g/L. After 25.1 hours, the succinic acid concentration was 36.1 g/L, the glucose concentration was 2.2 g/L, and the xylose concentration was 13.6 g/L. The results are shown in Table 4.

Comparative Example 1-5

Comparative Example 1-5 was conducted in the same manner as in Example 1-6 except that a substrate solution was produced by mixing 58 g of the treated saccharide solution 1-7 produced in Comparative Example 1-2, 7 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 18.9 hours, the succinic acid concentration was 23.7 g/L, the glucose concentration was 24.6 g/L, and the xylose concentration was 15.0 g/L. After 25.1 hours, the succinic acid concentration was 26.0 g/L, the glucose concentration was 20.9 g/L, and the xylose concentration was 13.1 g/L. The results are shown in Table 4.

TABLE 4

| | Treatment method of saccharide solution (saccharide solution used) | Period (hr) | Succinic acid concentration (g/L) | Glucose concentration (g/L) | Xylose concentration (g/L) |
|---|---|---|---|---|---|
| Example 1-7 | heat treatment → reduction (treated saccharide solution 1-2) | 18.9<br>25.1 | 32.0<br>36.1 | 8.3<br>2.2 | 14.9<br>13.6 |
| Comparative Example 1-3 | heat treatment (saccharified solution 1-1) | 19.1<br>24.4 | 27.2<br>30.4 | 16.0<br>11.6 | 15.9<br>14.5 |
| Comparative Example 1-5 | reduction → heat treatment (treated saccharide solution 1-7) | 18.9<br>25.1 | 23.7<br>26.0 | 24.6<br>20.9 | 15.0<br>13.1 |

From Table 4, in Example 1-7, after 18.9 hours, the succinic acid concentration increased by 18% compared to that of Comparative Example 1-3, and the succinic acid concentration increased by 35% compared to that of Comparative Example 1-5. After 25.1 hours, the succinic acid concentration increased by 19% compared to that of Comparative Example 1-3, and the succinic acid concentration increased by 39% compared to that of Comparative Example 1-5.

From the above results, it has been elucidated that by reacting a reducing agent with a saccharide solution after heating the saccharide solution, the inhibition of the fermentation is reduced in degree, and the production rate of an organic compound increases. The effects cannot be obtained when the saccharide solution is heated after being reacted with the reducing agent.

Example 1-8

Example 1-8 was conducted in the same manner as in Example 1-6 except that a substrate solution was produced by mixing 56 g of the treated saccharide solution 1-3 produced in Example 1-3, 10 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 18.3 hours, the succinic acid concentration was 32.2 g/L, the glucose concentration was 7.1 g/L, and the xylose concentration was 16.1 g/L. After 25.6 hours, the succinic acid concentration was 37.3 g/L, the glucose concentration was 0.1 g/L, and the xylose concentration was 14.1 g/L.

Example 1-9

Example 1-9 was conducted in the same manner as in Example 1-6 except that a substrate solution was produced by mixing 56 g of the treated saccharide solution 1-4 produced in Example 1-4, 9 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 18.3 hours, the succinic acid concentration was 30.9 g/L, the glucose concentration was 9.1 g/L, and the xylose concentration was 16.5 g/L. After 25.6 hours, the succinic acid concentration was 36.2 g/L, the glucose concentration was 2.1 g/L, and the xylose concentration was 14.7 g/L.

Example 1-10

Example 1-10 was conducted in the same manner as in Example 1-6 except that a substrate solution was produced by mixing 56 g of the treated saccharide solution 1-5 produced in Example 1-5, 10 g of distilled water, 1 mL of the cell-suspending solution, 133 mg of an aqueous D-biotin solution (100 mg/L) and 133 mg of an aqueous thiamine hydrochloride solution (100 mg/L) in the reaction for producing succinic acid. The LC analysis was conducted under the same conditions as those in Example 1-6. As a result, after 18.3 hours, the succinic acid concentration was 36.6 g/L, the glucose concentration was 0.0 g/L, and the xylose concentration was 15.4 g/L. After 25.6 hours, the succinic acid concentration was 39.4 g/L, the glucose concentration was 0.0 g/L, and the xylose concentration was 12.8 g/L.

The results of the measurement of Examples 1-8 to 1-10 and Comparative Example 1-3 are shown in Table 5.

TABLE 5

| | Treatment method of saccharide solution (saccharide solution used) | Period (hr) | Succinic acid concentration (g/L) | Glucose concentration (g/L) | Xylose concentration (g/L) |
|---|---|---|---|---|---|
| Example 1-8 | heat treatment → reduction (treated saccharide solution 1-3) | 18.3 25.6 | 32.2 37.3 | 7.1 0.1 | 16.1 14.1 |
| Example 1-9 | heat treatment → reduction (treated saccharide solution 1-4) | 18.3 25.6 | 30.9 36.2 | 9.1 2.1 | 16.5 14.7 |
| Example 1-10 | heat treatment → reduction (treated saccharide solution 1-5) | 18.3 25.6 | 36.6 39.4 | 0.0 0.0 | 15.4 12.8 |
| Comparative Example 1-3 | heat treatment (saccharified solution 1-1) | 19.1 24.4 | 27.2 30.4 | 16.0 11.6 | 15.9 14.5 |

From Table 5, with the saccharide solution of Example 1-8, after 18.3 hours, the succinic acid concentration increased by 18% compared to that of Comparative Example 1-3. With the saccharide solution of Example 1-9, after 18.3 hours, the succinic acid concentration increased by 14% compared to that of Comparative Example 1-3. With the saccharide solution of Example 1-10, after 18.3 hours, the succinic acid concentration increased by 35% compared to that of Comparative Example 1-3. Also, with the saccharide solution of Example 1-8, after 25.6 hours, the succinic acid concentration increased by 23% compared to that of Comparative Example 1-3. With the saccharide solution of Example 1-9, after 25.6 hours, the succinic acid concentration increased by 19% compared to that of Comparative Example 1-3. With the saccharide solution of Example 1-10, after 25.6 hours, the succinic acid concentration increased by 30% compared to that of Comparative Example 1-3.

Examples 1-11 to 1-14 and Comparative Examples 1-6 to 1-10

Production Example 1-4

A saccharide solution was produced by dissolving 135.61 g of glucose, 2.70 g of furfural and 0.18 g of formic acid in 365 mL of ultrapure water. The saccharide solution is referred to as "a saccharide solution A" below.

The saccharide solution A was analyzed by LC under the LC measurement conditions 1 and 2. As a result, the glucose content was 26.4 mass %, and the furfural content was 6042 ppm. The results are shown in Table 6.

Production Example 1-5

Into a 100-mL medium bottle, 44.08 g of the saccharide solution A prepared in Production Example 1-4 was put, and the pH was adjusted at 8 using an aqueous 48 mass % NaOH solution, followed by heat sterilization at 121° C. for 20 minutes. The resultant solution is called "a heated saccharide solution B". The heated saccharide solution B was analyzed by LC in the same manner as in Production Example 1-4. As a result, the glucose content was 24.6 mass %, the fructose content was 0.9 mass %, the furfural content was 2898 ppm, and the pH was 2.81. The results are shown in Table 6.

Example 1-11

The heated saccharide solution B was obtained by heat-sterilizing the saccharide solution A prepared in Production Example 1-4 in the same manner as in Production Example 1-5. After cooling the solution to room temperature, 0.5856 g of an aqueous 49 mass % ammonium sulfite solution was added to 44.01 g of the heated saccharide solution B so that 1 Eq of the reducing agent reacted with furfural contained in the saccharide solution A before heating, and the mixture was stirred at 40° C. for an hour, thereby obtaining a treated saccharide solution 1-8. The treated saccharide solution 1-8 was analyzed by LC under the LC measurement conditions 1 and 2. As a result, the glucose content was 23.6 mass %, the fructose content was 1.9 mass %, the furfural content was 1652 ppm, and the pH was 3.40. The results are shown in Table 6.

Example 1-12

The heated saccharide solution B was obtained by heat-sterilizing the saccharide solution A prepared in Production Example 1-4 in the same manner as in Production Example 1-5. After cooling the solution to room temperature, 0.1558 g of sodium sulfite was added to 44.03 g of the heated saccharide solution B so that 0.5 Eq of the reducing agent reacted with furfural contained in the saccharide solution A before heating, and the mixture was stirred at 40° C. for an hour, thereby obtaining a treated saccharide solution 1-9. The treated saccharide solution 1-9 was analyzed by LC in the same manner as in Example 1-11. As a result, the glucose content was 24.4 mass %, the fructose content was 1.4 mass %, the furfural content was 2898 ppm, and the pH was 2.96. The results are shown in Table 6.

Comparative Example 1-6

The saccharide solution A prepared in Production Example 1-4 was put into a 100-mL medium bottle, and 0.5858 g of an aqueous 49 mass % ammonium sulfite solution was added to 43.97 g of the saccharide solution A so that 1 Eq of the reducing agent reacted with furfural contained in the saccharide solution A. The mixture was stirred at 40° C. for an hour, thereby conducting reduction. Then, the pH was adjusted at 8 using an aqueous 48 mass % NaOH solution, and heat sterilization was conducted at 121° C. for 20 minutes. The solution was cooled to room temperature, and a treated saccharide solution 1-10 was thus obtained. The treated saccharide solution 1-10 was analyzed by LC in the same manner as in Example 1-11. As a result, the glucose content was 24.8 mass %, the fructose content was 1.1 mass %, the furfural content was 2845 ppm, and the pH was 7.80. The results are shown in Table 6.

Comparative Example 1-7

The saccharide solution A prepared in Production Example 1-4 was put into a 100-mL medium bottle, and 0.1562 g of sodium sulfite was added to 44.02 g of the saccharide solution A so that 0.5 Eq of the reducing agent reacted with furfural contained in the saccharide solution A. The mixture was stirred at 40° C. for an hour, thereby conducting reduction. Then, the pH was adjusted at 8 using an aqueous 48 mass % NaOH solution, and heat sterilization was conducted at 121° C. for 20 minutes. The solution was cooled to room temperature, and a treated saccharide solution 1-11 was thus obtained. The treated saccharide solution 1-11 was analyzed by LC in the same manner as in Example 1-11. As a result, the glucose content was 19.2 mass %, the fructose content was 6.2 mass %, the furfural content was 3015 ppm, and the pH was 7.80. The results are shown in Table 6.

TABLE 6

| | | | Conditions of reduction | | | | Concentrations of components in saccharide solution | | |
| --- | --- | --- | --- | --- | --- | --- | --- | --- | --- |
| | Order of treatment | Conditions of heat treatment | Reducing agent | Amount (Eq) | Treatment temperature (° C.) | Treatment period (hr) | Glu (mass %) | Fru (mass %) | FRL (ppm) |
| Example 1-11 | heat treatment → reduction (treated saccharide solution 1-8) | 121° C. 20 min | $(NH_4)_2SO_3$ | 1 | 40 | 1 | 23.6 | 1.9 | 1652 |
| Example 1-12 | heat treatment → reduction (treated saccharide solution 1-9) | | $Na_2SO_3$ | 0.5 | 40 | 1 | 19.2 | 1.4 | 2898 |
| Production Example 1-4 | — (saccharide solution A) | — | — | — | — | — | 26.4 | 0.0 | 6042 |
| Production Example 1-5 | heat treatment (heated saccharide solution B) | | — | — | — | — | 24.6 | 0.9 | 2898 |
| Comparative Example 1-6 | reduction → heat treatment (treated saccharide solution 1-10) | | $(NH_4)_2SO_3$ | 1 | 40 | 1 | 24.8 | 1.1 | 2845 |
| Comparative Example 1-7 | reduction → heat treatment (treated saccharide solution 1-11) | | $Na_2SO_3$ | 0.5 | 40 | 1 | 24.4 | 6.2 | 3015 |

* In the table, Glu represents glucose, and Fru represents fructose.
* In the table, FRL represents furfural.

Example 1-13

Evaluation of Fermentative Production of Ethanol from Treated Saccharide Solution (A) Seed Culture Sixty grams of yeast extract were dissolved in 1000 mL of distilled water, and the mixture was heat-sterilized at 121° C. for 20 minutes and cooled to room temperature (hereinafter referred to as the medium (B)). Then, 10 mL of the medium (B) was put into a 200-mL Erlenmeyer flask, and 12 mL of an aqueous 42.5 mass % glucose solution and 8 mL of distilled water which had been sterilized in advance were added. *Saccharomyces cerevisiae* strain PE-2 (NCYC3233) was seeded therein and shake-cultured at 30° C. for 23.4 hours.

(B) Main Culture (Fermentative Production of Ethanol)

Into a 200-mL flask, 20 mL of the treated saccharide solution 1-8 prepared in Example 1-11 was put, and 10 mL of the medium (B) was added. The pH was adjusted at 4.5 by adding 1 mol/L sulfuric acid, and a main culture medium was thus produced. Cells were collected from the culture liquid obtained by the seed culture of (A) above by centrifugation (1000×g, five minutes), and 0.1 g of the cells in terms of the wet cell weight was seeded in the main culture medium and shake-cultured at 30° C. As a result, the OD (660 nm) after 20 hours of culture was 44.8. The culture supernatant was analyzed by LC under the LC measurement conditions 1 and 3. As a result, the ethanol concentration was 74.5 g/L, the glucose concentration was 1.2 g/L, and the fructose concentration was 2.3 g/L. The results are shown in Table 7.

Comparative Example 1-8

Comparative Example 1-8 was conducted in the same manner as in Example 1-13 except that the heated saccharide solution B prepared in Production Example 1-5 was used for the ethanol fermentation. As a result, the OD (660 nm) after 20 hours of culture was 19.7. The LC analysis was conducted in the same manner as in Example 1-13. As a result, the ethanol concentration was 27.8 g/L, the glucose concentration was 123.6 g/L, and the fructose concentration was 4.4 g/L. The results are shown in Table 7 and Table 8.

Comparative Example 1-9

Comparative Example 1-9 was conducted in the same manner as in Example 1-13 except that the treated saccharide solution 1-10 prepared in Comparative Example 1-6 was used for the ethanol fermentation. As a result, the OD (660 nm) after 20 hours of culture was 32.1. The LC analysis was conducted in the same manner as in Example 1-13. As a result, the ethanol concentration was 55.3 g/L, the glucose concentration was 58.7 g/L, and the fructose concentration was 4.1 g/L. The results are shown in Table 7.

TABLE 7

| | Treatment method of saccharide solution (saccharide solution used) | OD (660 nm) | Ethanol (g/L) | Glu (g/L) | Fru (g/L) |
|---|---|---|---|---|---|
| Example 1-13 | heat treatment → reduction (treated saccharide solution 1-8) | 44.8 | 74.5 | 1.2 | 2.3 |
| Comparative Example 1-8 | heat treatment (heated saccharide solution B) | 19.7 | 27.8 | 123.6 | 4.4 |
| Comparative Example 1-9 | reduction → heat treatment (treated saccharide solution 1-10) | 32.1 | 55.3 | 58.7 | 4.1 |

* In the table, Glu represents glucose, and Fru represents fructose.

From Table 7, in Example 1-13, the growth after 20 hours increased by 127% compared to that of Comparative Example 1-8 and by 40% compared to that of Comparative Example 1-9. Also, the ethanol concentration increased by 168% compared to that of Comparative Example 1-8 and by 35% compared to that of Comparative Example 1-9. From the above results, it has been elucidated that by reacting a reducing agent with a saccharide solution after heating the saccharide solution, the inhibition of the growth and the inhibition of the fermentation are reduced in degree, and the production rate of an organic compound increases. The effects cannot be obtained when the saccharide solution is heated after being reacted with the reducing agent.

Example 1-14

Example 1-14 was conducted in the same manner as in Example 1-13 except that the treated saccharide solution 1-9 prepared in Example 1-12 was used for the ethanol fermentation. As a result, the OD (660 nm) after 20 hours of culture was 39.6, the ethanol concentration was 68.2 g/L, the glucose concentration was 22.5 g/L, and the fructose concentration was 3.9 g/L. The results are shown in Table 8.

Comparative Example 1-10

Comparative Example 1-10 was conducted in the same manner as in Example 1-13 except that the treated saccharide solution 1-11 prepared in Comparative Example 1-7 was used for the ethanol fermentation. As a result, the OD (660 nm) after 20 hours of culture was 26.7, the ethanol concentration was 52.5 g/L, the glucose concentration was 43.7 g/L, and the fructose concentration was 23.3 g/L. The results are shown in Table 8.

TABLE 8

| | Treatment method of saccharide solution (saccharide solution used) | OD (660 nm) | Ethanol (g/L) | Glu (g/L) | Fru (g/L) |
|---|---|---|---|---|---|
| Example 1-14 | heat treatment → reduction (treated saccharide solution 1-9) | 39.6 | 68.2 | 22.5 | 3.9 |
| Comparative Example 1-8 | heat treatment (heated saccharide solution B) | 19.7 | 27.8 | 123.6 | 4.4 |

TABLE 8-continued

| | Treatment method of saccharide solution (saccharide solution used) | OD (660 nm) | Ethanol (g/L) | Glu (g/L) | Fru (g/L) |
|---|---|---|---|---|---|
| Comparative Example 1-10 | reduction → heat treatment (treated saccharide solution 1-11) | 26.7 | 52.5 | 43.7 | 23.3 |

* In the table, Glu represents glucose, and Fru represents fructose.

From Table 8, in Example 1-14, the growth after 20 hours increased by 101% compared to that of Comparative Example 1-8 and by 48% compared to that of Comparative Example 1-10. Also, the ethanol concentration increased by 145% compared to that of Comparative Example 1-8 and by 30% compared to that of Comparative Example 1-10. From the above results, it has been elucidated that by reacting a reducing agent with a saccharide solution after heating the saccharide solution, the inhibition of the growth and the inhibition of the fermentation are reduced in degree, and the production rate of an organic compound increases. The effects cannot be obtained when the saccharide solution is heated after being reacted with the reducing agent.

From the above results, it has been elucidated that by reacting a reducing agent with a saccharide solution after heating the saccharide solution, the inhibition of the fermentation is reduced in degree, and the production rate of an organic compound increases.

It has been elucidated that, when a model solution containing FRL is used for the reduction of the invention, the FRL amount can be reduced under a temperature condition of 25 to 60° C. and that the production rate of an organic compound increases when the treated saccharide solution is used. On the other hand, in case of an actual saccharified solution obtained using bagasse or the like, in addition to FRL and HMF which are measured, the amounts of water-soluble aldehydes such as glycolaldehyde, formaldehyde and acetaldehyde are often high. It is believed that the water-soluble aldehydes react with the reducing agent better than FRL or HMF and are reduced in amount and that the recovery of the results of fermentation which is equivalent to or more than the range of decrease in FRL or HMF amount is thus observed when the saccharified solution is used.

It is believed that fermentation inhibitors such as the carbonyl compounds are removed from a saccharide solution by forming reaction adducts with a reducing agent. It has been found that because the reaction adducts are unstable under high-temperature conditions and are degraded under the heating conditions for sterilizing the saccharide solution, it is more effective that the heat treatment step is conducted before the reduction step compared to the case where the heat treatment is conducted after the reduction step.

By the production method of the invention, fermentation inhibitors such as the carbonyl compounds can be removed while the sterilized state is maintained. Thus, it is believed that an organic compound can be produced efficiently even from a saccharide solution, preferably a saccharide solution containing a large amount of fermentation inhibitors such as the carbonyl compounds derived from a non-edible material.

Examples 2-1 to 2-16 and Comparative Example 2-1

Production Example 2-1

A saccharide solution was produced by dissolving 39.98 g of glucose, 5.02 g of xylose, 0.51 g of furfural, 1.50 g of glycolaldehyde dimer and 0.21 g of formic acid in 453 mL of ultrapure water. The saccharide solution is referred to as "a saccharide solution 2-1" below.

The saccharide solution 2-1 was analyzed by LC under the LC measurement conditions 1 and 2. As a result, the glucose content was 7.96 mass %, the xylose content was 1.01 mass %, the glycolaldehyde dimer content was 3120 ppm, the furfural content was 822 ppm, the formic acid content was 400 ppm, and the pH was 2.79.

Example 2-1

To 60.04 g of the saccharide solution 2-1 prepared in Production Example 2-1, 0.079 g of an aqueous 50 mass % ammonium sulfite solution was added at 40° C. so that 0.08 Eq of the reducing agent reacted with the carbonyl components except for the saccharides. The mixture was stirred at the same temperature of 40° C. for 30 minutes, and a reduced saccharide solution was obtained (hereinafter referred to as "a treated saccharide solution 2-1"). The treated saccharide solution 2-1 was analyzed by LC under the same conditions as those for the saccharide solution 2-1 to determine the amounts of the components contained. As a result, the glucose content was 7.98 mass %, the xylose content was 1.01 mass %, the glycolaldehyde dimer content was 2758 ppm, the furfural content was 818 ppm, the formic acid content was 416 ppm, and the pH was 3.55. The results are shown in Table 9.

Example 2-2

The reduction was conducted by the same method as that in Example 2-1 except that the amount of the aqueous 50 mass % ammonium sulfite solution used was changed in such a manner that 0.23 Eq of the reducing agent reacted with the carbonyl components except for the saccharides, and a reduced saccharide solution ("a treated saccharide solution 2-2" below) was obtained. The treated saccharide solution 2-2 was analyzed by LC under the same conditions as those in Example 2-1. As a result, the glucose content was 7.94 mass %, the xylose content was 1.01 mass %, the glycolaldehyde dimer content was 2057 ppm, the furfural content was 808 ppm, the formic acid content was 395 ppm, and the pH was 6.49. The results are shown in Table 9.

Example 2-3

The reduction was conducted by the same method as that in Example 2-1 except that the amount of the aqueous 50 mass % ammonium sulfite solution used was changed in such a manner that 0.53 Eq of the reducing agent reacted with the carbonyl components except for the saccharides, and a reduced saccharide solution ("a treated saccharide solution 2-3" below) was obtained. The treated saccharide solution 2-3 was analyzed by LC under the same conditions as those in Example 2-1. As a result, the glucose content was 7.94 mass %, the xylose content was 1.01 mass %, the glycolaldehyde dimer content was 831 ppm, the furfural content was 727 ppm, the formic acid content was 406 ppm, and the pH was 7.85. The results are shown in Table 9.

Example 2-4

The reduction was conducted by the same method as that in Example 2-1 except that the amount of the aqueous 50 mass % ammonium sulfite solution used was changed in such a manner that 1.02 Eq of the reducing agent reacted with the carbonyl components except for the saccharides, and a reduced saccharide solution ("a treated saccharide solution 2-4" below) was obtained. The treated saccharide solution 2-4 was analyzed by LC under the same conditions as those in Example 2-1. As a result, the glucose content was 7.84 mass %, the xylose content was 1.12 mass %, the glycolaldehyde dimer content was 112 ppm, the furfural content was 226 ppm, the formic acid content was 367 ppm, and the pH was 7.82. The results are shown in Table 9.

Example 2-5

The reduction was conducted by the same method as that in Example 2-1 except that the amount of the aqueous 50 mass % ammonium sulfite solution used was changed in such a manner that 1.52 Eq of the reducing agent reacted with the carbonyl components except for the saccharides, and a reduced saccharide solution ("a treated saccharide solution 2-5" below) was obtained. The treated saccharide solution 2-5 was analyzed by LC under the same conditions as those in Example 2-1. As a result, the glucose content was 7.77 mass %, the xylose content was 1.02 mass %, the glycolaldehyde dimer content was 34 ppm, the furfural content was 548 ppm, the formic acid content was 355 ppm, and the pH was 7.64. The results are shown in Table 9.

Example 2-6

The treatment with the reducing agent was conducted by the same method as that in Example 2-1 except that the amount of the aqueous 50 mass % ammonium sulfite solution used was changed in such a manner that 2.05 Eq of the reducing agent reacted with the carbonyl components except for the saccharides, and a reduced saccharide solution ("a treated saccharide solution 2-6" below) was obtained. The treated saccharide solution 2-6 was analyzed by LC under the same conditions as those in Example 2-1. As a result, the glucose content was 7.67 mass %, the xylose content was 0.95 mass %, the glycolaldehyde dimer content was 24 ppm, the furfural content was 660 ppm, the formic acid content was 349 ppm, and the pH was 7.57. The results are shown in Table 9.

Example 2-7

The reduction was conducted by the same method as that in Example 2-4 except that the treatment temperature was changed to 25° C., and a reduced saccharide solution ("a treated saccharide solution 2-7" below) was obtained. The treated saccharide solution 2-7 was analyzed by LC. As a result, the glucose content was 7.80 mass %, the xylose content was 1.11 mass %, the glycolaldehyde dimer content was 58 ppm, the furfural content was 416 ppm, the formic acid content was 393 ppm, and the pH was 7.85. The results are shown in Table 9.

Example 2-8

The treatment with the reducing agent was conducted by the same method as that in Example 2-4 except that the treatment temperature was changed to 60° C., and a reduced saccharide solution ("a treated saccharide solution 2-8" below) was obtained. The treated saccharide solution 2-8 was analyzed by LC. As a result, the glucose content was 7.84 mass %, the xylose content was 1.04 mass %, the glycolaldehyde dimer content was 184 ppm, the furfural content was 174 ppm, the formic acid content was 429 ppm, and the pH was 7.76. The results are shown in Table 9.

TABLE 9

| | | Treatment temperature (° C.) | Amount of reducing agent (Eq) | Concentrations of components in saccharide solution | | | | | |
|---|---|---|---|---|---|---|---|---|---|
| | | | | Glu (mass %) | Xyl (mass %) | GAL (ppm) | FRL (ppm) | FA (ppm) | pH |
| Production Example 2-1 | saccharide solution 2-1 | — | — | 7.96 | 1.01 | 3120 | 822 | 400 | 2.79 |
| Example 2-1 | treated saccharide solution 2-1 | 40 | 0.08 | 7.98 | 1.01 | 2758 | 818 | 416 | 3.55 |
| Example 2-2 | treated saccharide solution 2-2 | 40 | 0.23 | 7.94 | 1.01 | 2057 | 808 | 395 | 6.49 |
| Example 2-3 | treated saccharide solution 2-3 | 40 | 0.53 | 7.94 | 1.01 | 831 | 727 | 406 | 7.85 |
| Example 2-4 | treated saccharide solution 2-4 | 40 | 1.02 | 7.84 | 1.12 | 112 | 226 | 367 | 7.82 |
| Example 2-5 | treated saccharide solution 2-5 | 40 | 1.52 | 7.77 | 1.02 | 34 | 548 | 355 | 7.64 |
| Example 2-6 | treated saccharide solution 2-6 | 40 | 2.05 | 7.67 | 0.95 | 24 | 660 | 349 | 7.57 |
| Example 2-7 | treated saccharide solution 2-7 | 25 | 1.02 | 7.80 | 1.11 | 58 | 416 | 393 | 7.85 |
| Example 2-8 | treated saccharide solution 2-8 | 60 | 1.02 | 7.84 | 1.04 | 184 | 174 | 429 | 7.76 |

* In the table, Glu represents glucose, Xyl represents xylose, GAL represents glycolaldehyde dimer, FRL represents furfural, and FA represents formic acid.

From Table 9, it has been found that carbonyl compounds such as glycolaldehyde, furfural and formic acid can be removed by the treatment method of the invention. It has been elucidated that carbonyl compounds except for saccharides can be removed efficiently using the reducing agent of the invention and that the treatment method of the invention can remove carbonyl compounds except for saccharides effectively at a wide range of temperature.

Production Example 2-2

A xylose isomerase gene- and xylulokinase gene-introduced strain was produced in the same manner as in Production Example 1-3.

Example 2-9

Evaluation of Fermentative Production of Saccharide Solution (A) Seed Culture

A thousand milliliters of the medium A [4 g of urea, 14 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate pentahydrate, 200 µg of D-biotin, 200 µg of thiamine hydrochloride, 1 g of yeast extract and 1 g of casamino acid dissolved in 1,000 mL of distilled water] were heat-sterilized at 121° C. for 20 minutes and cooled to room temperature. Then, 15 mL of the medium was put into a 200-mL Erlenmeyer flask, and 600 µl of an aqueous 50% glucose solution which had been sterilized in advance was added. *Brevibacterium flavum* strain MJ233/XylAB/PC-4/ΔLDH produced by the step of Production Example 2-2 corresponding to Production Example 1-3 (D) was seeded and shake-cultured at 30° C. for 4.8 hours.

(B) Main Culture

To a 500-mL Erlenmeyer flask, 100 mL of the medium A was put, and 4 mL of an aqueous 50% glucose solution which had been sterilized in advance was added. Then, the culture liquid obtained by the seed culture of (A) above was seeded in such a manner that the O.D. (660 nm) became 0.05, and the cells were shake-cultured at 30° C. for 20.0 hours.

(C) Reaction for Producing Succinic Acid

Cells were collected from the culture liquid obtained by the main culture of (B) above by centrifugation at 5,000×g for seven minutes and suspended in a cell-suspending solution [1 g of magnesium sulfate heptahydrate, 40 mg of ferrous sulfate heptahydrate, 40 mg of manganese sulfate pentahydrate, 400 µg of D-biotin, 400 µg of thiamine hydrochloride, 0.8 g of monoammonium phosphate, 0.8 g of diammonium phosphate and 1 g of potassium chloride dissolved in 1000 mL of distilled water] in such a manner that the O.D. (660 nm) became 20. Subsequently, 2.2 mL of the treated saccharide solution 2-1 produced in Example 2-1, 0.3 g of ammonium hydrogen carbonate and 2.8 mL of distilled water were mixed to prepare a substrate solution. In a 5-mL reactor, 0.5 mL of the cell-suspending solution and 0.5 mL of the substrate solution were mixed and reacted under anaerobic conditions at 40° C. The culture supernatant was analyzed by LC under the LC measurement conditions 1 and 2. As a result, after six hours, the concentration of succinic acid accumulated was 7.6 g/L, the glucose concentration was 5.3 g/L, and the xylose concentration was 1.9 g/L. The results are shown in Table 10.

Comparative Example 2-1

Comparative Example 2-1 was conducted in the same manner as in Example 2-9 except that a substrate solution was prepared by mixing 2.2 mL of the saccharide solution 2-1 produced in Production Example 2-1, 0.3 g of ammonium hydrogen carbonate and 2.8 mL of distilled water in the reaction for producing succinic acid. The LC analysis was conducted in the same manner as in Example 2-9. As a result, after six hours, the concentration of succinic acid accumulated was 7.1 g/L, the glucose concentration was 5.8 g/L, and the xylose concentration was 1.9 g/L. The results are shown in Table 10.

Example 2-10

Example 2-10 was conducted in the same manner as in Example 2-9 except that a substrate solution was prepared by mixing 2.2 mL of the treated saccharide solution 2-2 produced in Example 2-2, 0.3 g of ammonium hydrogen carbonate and 2.8 mL of distilled water in the reaction for producing succinic acid. The LC analysis was conducted in the same manner as in Example 2-9. As a result, after six hours, the concentration of succinic acid accumulated was 8.2 g/L, the glucose concentration was 4.3 g/L, and the xylose concentration was 2.0 g/L. The results are shown in Table 10.

Example 2-11

Example 2-11 was conducted in the same manner as in Example 2-9 except that a substrate solution was prepared by mixing 2.2 mL of the treated saccharide solution 2-3 produced in Example 2-3, 0.3 g of ammonium hydrogen carbonate and 2.8 mL of distilled water in the reaction for producing succinic acid. The LC analysis was conducted in the same manner as in Example 2-9. As a result, after six hours, the concentration of succinic acid accumulated was 9.0 g/L, the glucose concentration was 2.9 g/L, and the xylose concentration was 2.0 g/L. The results are shown in Table 10.

Example 2-12

Example 2-12 was conducted in the same manner as in Example 2-9 except that a substrate solution was prepared by mixing 2.2 mL of the treated saccharide solution 2-4 produced in Example 2-4, 0.3 g of ammonium hydrogen carbonate and 2.8 mL of distilled water in the reaction for producing succinic acid. The LC analysis was conducted in the same manner as in Example 2-9. As a result, after six hours, the concentration of succinic acid accumulated was 9.2 g/L, the glucose concentration was 2.4 g/L, and the xylose concentration was 2.0 g/L. The results are shown in Table 10.

Example 2-13

Example 2-13 was conducted in the same manner as in Example 2-9 except that a substrate solution was prepared by mixing 2.3 mL of the treated saccharide solution 2-5 produced in Example 2-5, 0.3 g of ammonium hydrogen carbonate and 2.7 mL of distilled water in the reaction for producing succinic acid. The LC analysis was conducted in the same manner as in Example 2-9. As a result, after six hours, the concentration of succinic acid accumulated was 8.3 g/L, the glucose concentration was 3.1 g/L, and the xylose concentration was 1.9 g/L. The results are shown in Table 10.

Example 2-14

Example 2-14 was conducted in the same manner as in Example 2-9 except that a substrate solution was prepared by mixing 2.3 mL of the treated saccharide solution 2-6 produced in Example 2-6, 0.3 g of ammonium hydrogen carbonate and 2.7 mL of distilled water in the reaction for producing succinic acid. The LC analysis was conducted in the same manner as in Example 2-9. As a result, after six hours, the concentration of succinic acid accumulated was 7.4 g/L, the glucose concentration was 4.7 g/L, and the xylose concentration was 2.0 g/L. The results are shown in Table 10.

Example 2-15

Example 2-15 was conducted in the same manner as in Example 2-9 except that a substrate solution was prepared by mixing 2.2 mL of the treated saccharide solution 2-7 produced in Example 2-7, 0.3 g of ammonium hydrogen carbonate and 2.8 mL of distilled water in the reaction for producing succinic acid. The LC analysis was conducted in the same manner as in Example 2-9. As a result, after six hours, the concentration of succinic acid accumulated was 9.2 g/L, the glucose concentration was 2.6 g/L, and the xylose concentration was 2.0 g/L. The results are shown in Table 10.

Example 2-16

Example 2-16 was conducted in the same manner as in Example 2-9 except that a substrate solution was prepared by mixing 2.3 mL of the treated saccharide solution 2-8 produced in Example 2-8, 0.3 g of ammonium hydrogen carbonate and 2.7 mL of distilled water in the reaction for producing succinic acid. The LC analysis was conducted in the same manner as in Example 2-9. As a result, after six hours, the concentration of succinic acid accumulated was 9.3 g/L, the glucose concentration was 2.0 g/L, and the xylose concentration was 2.0 g/L. The results are shown in Table 10.

TABLE 10

| | | Reduction temperature (° C.) | Amount of reducing agent (Eq) | Accumulated concentrations | | |
|---|---|---|---|---|---|---|
| | | | | Succinic acid (g/L) | Glucose (g/L) | Xylose (g/L) |
| Example 2-9 | treated saccharide solution 2-1 | 40 | 0.08 | 7.6 | 5.3 | 1.9 |
| Example 2-10 | treated saccharide solution 2-2 | 40 | 0.23 | 8.2 | 4.3 | 2.0 |
| Example 2-11 | treated saccharide solution 2-3 | 40 | 0.53 | 9.0 | 2.9 | 2.0 |
| Example 2-12 | treated saccharide solution 2-4 | 40 | 1.02 | 9.2 | 2.4 | 2.0 |
| Example 2-13 | treated saccharide solution 2-5 | 40 | 1.52 | 8.3 | 3.1 | 1.9 |
| Example 2-14 | treated saccharide solution 2-6 | 40 | 2.05 | 7.4 | 4.7 | 2.0 |
| Example 2-15 | treated saccharide solution 2-7 | 25 | 1.02 | 9.2 | 2.6 | 2.0 |
| Example 2-16 | treated saccharide solution 2-8 | 60 | 1.02 | 9.3 | 2.0 | 2.0 |
| Comparative Example 2-1 | saccharide solution 2-1 | — | — | 7.1 | 5.8 | 1.9 |

From Table 10, in Example 2-9, in which the treated saccharide solution 2-1 of Example 2-1 was used, the succinic acid concentration increased by 6% compared to that of Comparative Example 2-1, in which the saccharide solution 2-1 of Production Example 2-1 was used.

Similarly, in Example 2-10, in which the treated saccharide solution 2-2 of Example 2-2 was used, the succinic acid concentration increased by 15% compared to that of Comparative Example 2-1.

In Example 2-11, in which the treated saccharide solution 2-3 of Example 2-3 was used, the succinic acid concentration increased by 27% compared to that of Comparative Example 2-1.

In Example 2-12, in which the treated saccharide solution 2-4 of Example 2-4 was used, the succinic acid concentration increased by 29% compared to that of Comparative Example 2-1.

In Example 2-13, in which the treated saccharide solution 2-5 of Example 2-5 was used, the succinic acid concentration increased by 16% compared to that of Comparative Example 2-1.

In Example 2-14, in which the treated saccharide solution 2-6 of Example 2-6 was used, the succinic acid concentration increased by 4% compared to that of Comparative Example 2-1.

It has been elucidated that the production rate of succinic acid increases when a saccharide solution from which a large amount of glycolaldehyde or the like has been removed by the treatment with a reducing agent of the invention is used.

Furthermore, in Example 2-15, in which the treated saccharide solution 2-7 of Example 2-7 was used, the succinic acid concentration increased by 29% compared to that of Comparative Example 2-1.

In Example 2-16, in which the treated saccharide solution 2-8 of Example 2-8 was used, the succinic acid concentration increased by 31% compared to that of Comparative Example 2-1.

It has been elucidated that when the reduction of the invention is conducted, a large amount of glycolaldehyde or the like can be removed under a temperature condition of 25 to 60° C. and that the production rate of succinic acid increases when the treated saccharide solution is used.

The invention has been explained in detail referring to specific embodiments, but it is obvious to one skilled in the art that various changes and modifications can be added without departing from the spirit and the scope of the invention. The present application is based on a Japanese patent application filed on Mar. 13, 2014 (JP2014-050704), a Japanese patent application filed on Jul. 10, 2014 (JP2014-142566) and a Japanese patent application filed on Dec. 4, 2014 (JP2014-246140), and the contents thereof are incorporated herein by reference.

INDUSTRIAL APPLICABILITY

According to the method for treating a saccharide solution of invention 1, the amount of a fermentation inhibitor contained in a saccharide solution can be reduced. Thus, when the saccharide solution obtained by the method is used for a fermentative production process using a microorganism, the target organic compound can be obtained at a high yield.

The treated saccharide solution of invention 1 can improve the production efficiency of a microorganism in the production of an organic compound through fermentative production.

By the method for producing an organic compound of invention 1, a desired organic compound can be produced with high production efficiency through relatively simple treatment.

By the culture method of invention 1, the amount of a fermentation inhibitor in a fermentative production process can be reduced. Thus, the multiplication amount and the multiplication rate of a microorganism can be increased, and the fermentative productivity can be thus improved.

According to the method for treating a saccharide of invention 2, the amount of a carbonyl compound except for the saccharide contained in a saccharide solution can be reduced efficiently. Thus, when the saccharide solution obtained by the method is used for a fermentative production process using a microorganism, the target organic compound can be obtained efficiently, and the yield thereof can be improved.

The reduced saccharide solution of invention 2 can improve the production efficiency of a microorganism in the production of an organic compound through fermentative production and prevent the coloration of the organic compound, which is the product, when used for a chemical conversion process.

The invention claimed is:

1. A method for treating a saccharide solution, comprising:
heating the saccharide solution at a temperature of 100° C. to 180° C., to obtain a heated saccharide solution; and
reacting a reducing agent with the heated saccharide solution.

2. The method according to claim 1,
wherein the saccharide solution comprises a monosaccharide, a disaccharide, or both.

3. The method according to claim 1, wherein a pH of the saccharide solution during the reacting is 2 to 8.

4. The method according to claim 1, wherein a temperature of the saccharide solution during the reacting is 20° C. to 70° C.

5. The method according to claim 1, wherein the reducing agent is at least one compound selected from the group consisting of a sulfurous acid compound, a hyposulfurous acid compound, and a thiosulfuric acid compound.

6. The method according to claim 1, wherein an amount of the reducing agent used is 0.05 mass % to 2.0 mass % based on a mass of the saccharide contained in the saccharide solution.

7. The method according to claim 1, wherein the heating of the saccharide solution is from one minute to 20 hours.

8. A method for producing an organic compound, comprising:
performing the method of claim 1 to obtain a reduced saccharide solution; and
contacting a microorganism capable of producing organic matter with an organic raw material comprising the reduced saccharide solution.

9. A method for producing an organic compound, comprising:
   heating a saccharide solution at a temperature of 100° C. to 180° C., to obtain a heated saccharide solution;
   reacting a reducing agent with the heated saccharide solution, to obtain a treated saccharide solution; and
   culturing a microorganism capable of producing organic matter in a medium comprising the treated saccharide solution as a carbon source.

10. The method of claim 1,
    wherein the reducing agent is an ionic compound,
    the ionic compound comprises: an anion containing one or more kinds of sulfur having an oxidation number selected from the group consisting of −2, +2, +3 and +4; and ammonium ion, and
    the reducing agent reduces a carbonyl compound except for a saccharide contained in the saccharide solution.

* * * * *

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: synthetic primer

<400> SEQUENCE: 1
aaaggatcca tcacccgcgg cattacctg                                      29

<210> SEQ ID NO 2
<211> LENGTH: 40
<212> TYPE: DNA
<213> ORGANISM: Artificial Sequence
<220> FEATURE:
<223> OTHER INFORMATION: synthetic primer

<400> SEQUENCE: 2
tttgggcccg tcgactgaga tatatagatg tgaattatcc                          40

<210> SEQ ID NO 3
<211> LENGTH: 38
<212> TYPE: DNA
<213> ORGANISM: Artificial Sequence
<220> FEATURE:
<223> OTHER INFORMATION: synthetic primer

<400> SEQUENCE: 3
cgaggggtcg aggattctgg ggaggatcga gtggattc                            38
```

```
<210> SEQ ID NO 4
<211> LENGTH: 38
<212> TYPE: DNA
<213> ORGANISM: Artificial Sequence
<220> FEATURE:
<223> OTHER INFORMATION: synthetic primer

<400> SEQUENCE: 4
tctagagtcg aggatggtga ccatgatgca ggatggag                              38

<210> SEQ ID NO 5
<211> LENGTH: 22
<212> TYPE: DNA
<213> ORGANISM: Artificial Sequence
<220> FEATURE:
<223> OTHER INFORMATION: synthetic primer

<400> SEQUENCE: 5
gtacctgcag gatgagcggg ct                                              22

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
cacccggtca ggcaggggat aac                                             23

<210> SEQ ID NO 7
<211> LENGTH: 24
<212> TYPE: DNA
<213> ORGANISM: Artificial Sequence
<220> FEATURE:
<223> OTHER INFORMATION: synthetic primer

<400> SEQUENCE: 7
aatcaggaag tgggatcgaa aatg                                            24

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
ccgccaacta gacaccaaag attc                                            24
```